US007285384B2

(12) United States Patent
Fan et al.

(10) Patent No.: US 7,285,384 B2
(45) Date of Patent: Oct. 23, 2007

(54) PARALLEL GENOTYPING OF MULTIPLE PATIENT SAMPLES

(75) Inventors: Jian-Bing Fan, San Diego, CA (US); Mark S. Chee, Del Mar, CA (US)

(73) Assignee: Illuminia, Inc., San Diego, CA (US)

( * ) Notice: Subject to any disclaimer, the term of this patent is extended or adjusted under 35 U.S.C. 154(b) by 0 days.

(21) Appl. No.: 09/785,514

(22) Filed: Feb. 16, 2001

(65) Prior Publication Data

US 2002/0001801 A1 Jan. 3, 2002

Related U.S. Application Data

(60) Provisional application No. 60/182,955, filed on Feb. 16, 2000.

(51) Int. Cl.
| | | |
|---|---|---|
| C12Q 1/68 | (2006.01) | |
| C12M 1/36 | (2006.01) | |
| C07H 21/04 | (2006.01) | |
| C12P 19/34 | (2006.01) | |

(52) U.S. Cl. .......................... 435/6; 435/91.1; 435/91.2; 435/283.1; 435/267.2; 536/22.1; 536/24.3; 536/24.33

(58) Field of Classification Search ................... 435/6, 435/91.1, 91.2, 7.1, 283.1, 285.2, 286.5; 536/24.3, 23.1; 935/6; 436/518; 530/35.1
See application file for complete search history.

(56) References Cited

U.S. PATENT DOCUMENTS

| 4,200,110 A | 4/1980 | Peterson et al. |
|---|---|---|
| 4,499,052 A | 2/1985 | Fulwyler |

(Continued)

FOREIGN PATENT DOCUMENTS

| EP | 0 269 764 | | 6/1988 |
|---|---|---|---|
| EP | 0 392 546 | | 10/1990 |
| EP | 0392546 | A2 * | 10/1990 |
| EP | 0 478 319 | | 4/1992 |
| EP | 0 723 146 | | 7/1996 |
| WO | WO 89/11101 | | 11/1989 |
| WO | WO 93/02360 | | 2/1993 |
| WO | WO 93/25563 | A1 | 12/1993 |
| WO | WO 94/02515 | A1 | 2/1994 |
| WO | WO 95/16918 | A1 | 6/1995 |
| WO | WO 95/21271 | A1 | 8/1995 |
| WO | WO 96/03212 | | 2/1996 |
| WO | WO 96/15271 | A1 | 5/1996 |
| WO | WO 96/30392 | A1 | 10/1996 |
| WO | WO 97/14028 | | 4/1997 |
| WO | WO 97/14928 | | 4/1997 |
| WO | WO 97/31256 | A2 | 8/1997 |
| WO | WO 97/40385 | | 10/1997 |
| WO | WO 97/45559 | A1 | 12/1997 |
| WO | WO 97/46704 | A1 | 12/1997 |
| WO | WO 98/04746 | A1 | 2/1998 |
| WO | WO 98/13523 | A1 | 4/1998 |
| WO | WO 98/31836 | A1 | 7/1998 |
| WO | WO 98/40726 | | 9/1998 |
| WO | WO 98/50782 | | 11/1998 |
| WO | WO 98/53093 | | 11/1998 |
| WO | WO 98/53300 | | 11/1998 |
| WO | WO 99/18434 | | 4/1999 |
| WO | WO 99/39001 | A2 | 8/1999 |
| WO | WO 99/60170 | | 11/1999 |
| WO | WO 99/64867 | A1 | 12/1999 |
| WO | WO 99/67414 | | 12/1999 |
| WO | WO 99/67641 | | 12/1999 |
| WO | WO 00/04372 | | 1/2000 |
| WO | WO 00/13004 | | 3/2000 |
| WO | WO 00/16101 | | 3/2000 |
| WO | WO 00/39587 | | 7/2000 |
| WO | WO 00/47996 | | 8/2000 |
| WO | WO 00/48000 | | 9/2000 |
| WO | WO 00/58516 | A2 | 10/2000 |
| WO | WO 00/63437 | | 10/2000 |
| WO | WO 00/71243 | | 11/2000 |
| WO | WO 00/71992 | A1 | 11/2000 |
| WO | WO 00/71995 | | 11/2000 |
| WO | WO 00/75373 | | 12/2000 |

OTHER PUBLICATIONS

Abel et al., "Fiber–Optic Evanescent Wave Biosensor for the Detection of Oligonucleotides," Anal. Chem. 68:2905–2912 (1996).
Anonymous, "Microsphere Selection Guide," Bandg Laboratories, (Fisher, In) Sep. 1998.
Anonymous, "Fluorescent Microspheres," Tech. Note 19, Bang Laboratories, (Fishers, In) Feb. 1997.
Bangs, L.B., "Immunological Applications of Microspheres," The Latex Course, Bangs Laboratories (Carmel, IN) Apr. 1996.
Barnard et al., "A Fibre–Optic Chemical Sensor with Discrete Sensing Sites," Nature, 353:338–340 (Sep. 1991).
Chen et al., "A Microsphere–Based Assay for Multiplexed Single Nucleotide Polymorphism Analysis Using Single Base Chain Extension," Genome Research, 10(4):549–557 (2000).
Czarnik, "Illuminating the SNP Genomic Code," Modern Drug Discovery, 1(2): 49–55 (1998).
Drmanac, R. et al., "Sequencing by Oligonucleotide Hybridization: A Promising Framework in Decoding of the Genome Program," The First International Conference on Electrophoresis, Supercomputing and the Human Genome, Proceeding os th Apr. 10–13, 1990 Conference at Florida State University. Ed. C. Cantor and H. Lim.
Drmanac, R. et al., "Prospects for a Miniaturized, Simplified and Frugal Human Genome Project," Scientia Yugoslavica, 16(1–2):97–107 (1990).

(Continued)

*Primary Examiner*—B J Forman
(74) *Attorney, Agent, or Firm*—David A. Gay; McDermott, Will & Emery

(57) ABSTRACT

The present invention relates to parallel genotyping (or other sample analysis) of multiple patients by direct sample immobilization onto microspheres of an array. The patient beads can then be used in a variety of target analyte analyses.

10 Claims, 4 Drawing Sheets

U.S. PATENT DOCUMENTS

| | | | |
|---|---|---|---|
| 4,682,895 A | 7/1987 | Costello | |
| 4,785,814 A | 11/1988 | Kane | |
| 4,822,746 A | 4/1989 | Walt | |
| 4,824,789 A | 4/1989 | Yafuso et al. | |
| 4,999,306 A | 3/1991 | Yafuso et al. | |
| 5,002,867 A | 3/1991 | Macevicz | |
| 5,028,545 A | 7/1991 | Soini | |
| 5,105,305 A | 4/1992 | Betzig et al. | |
| 5,114,864 A | 5/1992 | Walt | |
| 5,132,242 A | 7/1992 | Cheung | |
| 5,143,853 A | 9/1992 | Walt | |
| 5,194,300 A | 3/1993 | Cheung | |
| 5,244,636 A | 9/1993 | Walt et al. | |
| 5,244,813 A | 9/1993 | Walt et al. | |
| 5,250,264 A | 10/1993 | Walt et al. | |
| 5,252,494 A | 10/1993 | Walt | |
| 5,254,477 A | 10/1993 | Walt | |
| 5,298,741 A | 3/1994 | Walt et al. | |
| 5,302,509 A | 4/1994 | Cheeseman | |
| 5,320,814 A | 6/1994 | Walt et al. | |
| 5,357,590 A | 10/1994 | Auracher | |
| 5,380,489 A | 1/1995 | Sutton et al. | |
| 5,435,724 A | 7/1995 | Goodman et al. | |
| 5,474,895 A | 12/1995 | Ishii et al. | |
| 5,481,629 A | 1/1996 | Tabuchi | |
| 5,494,798 A | 2/1996 | Gerdt et al. | |
| 5,494,810 A | 2/1996 | Barany et al. | |
| 5,496,997 A | 3/1996 | Pope | |
| 5,512,490 A | 4/1996 | Walt et al. | |
| 5,516,635 A | 5/1996 | Ekins et al. | |
| 5,518,883 A | 5/1996 | Soini | |
| 5,565,324 A | 10/1996 | Still et al. | |
| 5,573,909 A | 11/1996 | Singer et al. | |
| 5,575,849 A | 11/1996 | Honda et al. | |
| 5,604,097 A | 2/1997 | Brenner | |
| 5,632,957 A | 5/1997 | Heller et al. | |
| 5,633,972 A | 5/1997 | Walt et al. | |
| 5,639,603 A | 6/1997 | Dower et al. | |
| 5,656,241 A | 8/1997 | Seifert et al. | |
| 5,679,524 A | 10/1997 | Nikiforov et al. | |
| 5,690,894 A | 11/1997 | Pinkel et al. | |
| 5,763,175 A | 6/1998 | Brenner | |
| 5,780,231 A | 7/1998 | Brenner | |
| 5,795,714 A | 8/1998 | Cantor et al. | |
| 5,814,524 A | 9/1998 | Walt et al. | |
| 5,830,711 A | 11/1998 | Barany et al. | |
| 5,840,256 A | 11/1998 | Demers et al. | |
| 5,846,719 A | * 12/1998 | Brenner et al. | 435/6 |
| 5,854,684 A | 12/1998 | Stabile et al. | |
| 5,856,083 A | 1/1999 | Chelsky et al. | |
| 5,858,732 A | 1/1999 | Solomon et al. | |
| 5,863,708 A | 1/1999 | Zanzucchi et al. | |
| 5,888,723 A | 1/1999 | Zanzucchi et al. | |
| 5,900,481 A | 5/1999 | Lough et al. | |
| 5,976,797 A | 11/1999 | Mitsuhashi | |
| 6,013,456 A | 1/2000 | Akhavan-Tafti | |
| 6,023,540 A | 2/2000 | Walt et al. | |
| 6,027,889 A | 2/2000 | Barany et al. | |
| 6,051,380 A | 4/2000 | Sosnowski et al. | |
| 6,054,564 A | 4/2000 | Barany et al. | |
| 6,083,763 A | 7/2000 | Balch | |
| 6,096,496 A | 8/2000 | Frankel | |
| 6,110,678 A | 8/2000 | Weisburg et al. | |
| 6,172,218 B1 | 1/2001 | Brenner | |
| 6,251,639 B1 | 6/2001 | Kurn | |
| 6,268,147 B1 | * 7/2001 | Beattie et al. | |
| 6,268,148 B1 | 7/2001 | Barany et al. | |
| 6,274,323 B1 | 8/2001 | Bruchez et al. | |
| 6,284,465 B1 | 9/2001 | Wolber | |
| 6,327,410 B1 | * 12/2001 | Walt et al. | 385/115 |
| 6,355,431 B1 | * 3/2002 | Chee et al. | |
| 6,429,027 B1 | * 8/2002 | Chee | 436/518 |

OTHER PUBLICATIONS

Drmanac, R. et al., "Sequencing by Hybridization (SBH) with Oligonucleotide Probes as an Integral Approach for the Analysis of Complex Genomes," International Journal of Genome Research, 1(1):59–79.

Drmanac, R. et al., "Sequencing by Hybridization," Automated DNA Sequencing and Analysis, ed. M. Adams, C. Fields and J. Venter. (1994).

Ferguson et al., "A Fiber–Optic DNA Biosensor Microarray for the Analysis of Gene Expression," Nature Biotechnology, 14:1681–1684 (1996).

Fuh et al., "Single Fibre Optic Fluorescence pH Probe," Analyst, 112:1159–1163 (1987).

Healey et al., "Improved Fiber–Optic Chemical Sensor for Penicillin," Anal. Chem. 67(24):4471–4476 (1995).

Healey et al., "Development of a Penicillin Biosensor Using a Single Optical Imaging Fiber," SPIE Proc. 2388:568–573 (1995).

Healey et al., "Fiberoptic DNA Sensor Array Capable of Detecting Point Mutations," Analytical Biochemistry, 251:270–279 (1997).

Hirschfeld et al., "Laser–Fiber–Optic "Optrode" for Real Time In Vivo Blood Carbon Dioxide Level Monitoring," Journal of Lightwave Technology, LT–5(7):1027–1033 (1987).

Iannone et al., "Multiplexed Single Nucleotide Polymorphism Genotyping by Oligonucleotide Ligation and Flow Cytometry," Cytometry, 39:131–140 (2000).

Michael et al., "Making Sensors out of Disarray: Optical Sensor Microarrays," Proc. SPIE, 3270: 34–41 (1998).

Michael et al., "Randomly Ordered Addressable High–Density Optical Sensor Arrays," Anal. Chem. 70(7): 1242–1248 (Apr. 1998).

Michael et al., "Fabrication of Micro– and Nanostructures Using Optical Imaging Fibers and there Use as Chemical Sensors," Proc. 3rd Intl. Symp., Microstructures and Microfabricated Systems, ed. P.J. Hesketh, et al., v.97–5, Electrochem. Soc., 152–157 (Aug. 1997).

Mignani, et al., "In–Vivo Biomedical Monitoring by Fiber–Optic System," Journal of Lightwave Technology, 13(7): 1396–1406 (1995).

Pantano et al., "Ordered Nanowell Arrays," Chem. Mater., 8(12): 2832–2835 (1996).

Peterson et al., "Fiber–Optic Sensors for Biomedical Applications," Science, 13:123–127 (1984).

Peterson, J. et al., "Fiber Optic pH Probe for Physiological Use," Anal. Chem., 52:864–869 (1980).

Piunno et al., "Fiber–Optic DNA Sensor for Fluorometric Nucleic Acid Determination," Anal. Chem., 67:2635–2643 (1995).

Pope, E. "Fiber Optic Chemical Microsensors Employing Optically Active Silica Microspehres," SPIE, 2388:245–256 (1995).

Strachan et al., "A Rapid General Method for the Identification of PCR Products Using a Fibre–Optic Biosensor and its Application to the Detection of Listeria," Letters in Applied Microbiology, 21:5–9 (1995).

Walt, D. "Fiber Optic Imaging Sensors," Accounts of Chemical Research, 31(5): 267–278 (1998).

Walt, "Fiber–Optic Sensors for Continuous Clinical Monitoring," Proc. IEEE, 80(6): 903–911 (1992).

Lyamichev et al., "Polymorphism identification and quantitative detection of genomic DNA by invasive cleavage of oligonucleotide probes," Nature Biotechnolgoy, 17:292–296 (1999).

Baner et al., "Signal amplification of padlock probes by rolling circle replication," Nucleic Acids Research, 26(22): 5073–5078 (1998).

Lizardi et al., "Mutation detection and single–molecule counting using isothermal rolling–circle amplification," Nature Genetics, 19: 225–232 (Jul. 1998).

Ronaghi et al., "A Sequencing Method Based on Real–Time Pyrophosphate." Science 281:363–365 (1998).

Shoemaker et al., "Quantitative phenotypic analysis of yeast deletion mutants using a highly parallel molecular bar–coding strategy." Nature Genetics. 14:450–456 (1996).

Syvanen. Anne–Christine. "From gels to chips: "Minisequencing" Primer Extension for Analysis of Point Mutations and Single Nucleotide Polymorphisms," Human Mutation. 13:1–10 (1999).

Ugozzoli et al., Detection of Specific Alleles by Using Allele-Specific Primer Extension Followed by Capture on Solid Support, GATA 9(4), 1992, pp. 107–112, Elsevier Science Publishing Co., Inc., New York, USA.

* cited by examiner

A. Positive control hybridization target

B. Negative control hybridization target

PARALLEL GENOTYPING OF MULTIPLE PATIENT SAMPLES

This application claims the benefit of provisional application Ser. No. 60/182,955 filed Feb. 16, 2000.

FIELD OF THE INVENTION

The present invention relates to parallel genotyping (or other sample analysis) of multiple patients by direct sample immobilization onto microspheres of an array. The patient beads can then be used in a variety of target analyte analyses.

BACKGROUND OF THE INVENTION

The detection of specific nucleic acids is an important tool for diagnostic medicine and molecular biology research. Gene probe assays currently play roles in identifying infectious organisms such as bacteria and viruses, in probing the expression of normal and mutant genes and identifying mutant genes such as oncogenes, in typing tissue for compatibility preceding tissue transplantation, in matching tissue or blood samples for forensic medicine, and for exploring homology among genes from different species.

Ideally, a gene probe assay should be sensitive, specific and easily automatable (for a review, see Nickerson, Current Opinion in Biotechnology 4:48–51 (1993)). The requirement for sensitivity (i.e. low detection limits) has been greatly alleviated by the development of the polymerase chain reaction (PCR) and other amplification technologies which allow researchers to amplify exponentially a specific nucleic acid sequence before analysis (for a review, see Abramson et al., Current Opinion in Biotechnology, 4:41–47 (1993)).

Specificity, in contrast, remains a problem in many currently available gene probe assays. The extent of molecular complementarity between probe and target defines the specificity of the interaction. Variations in the concentrations of probes, of targets and of salts in the hybridization medium, in the reaction temperature, and in the length of the probe may alter or influence the specificity of the probe/target interaction.

It may be possible under some circumstances to distinguish targets with perfect complementarity from targets with mismatches, although this is generally very difficult using traditional technology, since small variations in the reaction conditions will alter the hybridization. New experimental techniques for mismatch detection with standard probes include DNA ligation assays where single point mismatches prevent ligation and probe digestion assays in which mismatches create sites for probe cleavage.

Recent focus has been on the analysis of the relationship between genetic variation and phenotype by making use of polymorphic DNA markers. Previous work utilized short tandem repeats (STRs) as polymorphic positional markers; however, recent focus is on the use of single nucleotide polymorphisms (SNPs), which occur at an average frequency of more than 1 per kilobase in human genomic DNA. Some SNPs, particularly those in and around coding sequences, are likely to be the direct cause of therapeutically relevant phenotypic variants and/or disease predisposition. There are a number of well known polymorphisms that cause clinically important phenotypes; for example, the apoE2/3/4 variants are associated with different relative risk of Alzheimer's and other diseases (see Cordor et al., Science 261(1993). Multiplex PCR amplification of SNP loci with subsequent hybridization to oligonucleotide arrays has been shown to be an accurate and reliable method of simultaneously genotyping at least hundreds of SNPs; see Wang et al., Science, 280:1077 (1998); see also Schafer et al., Nature Biotechnology 16:33–39 (1998).

There are a variety of particular techniques that are used to detect sequence, including mutations and SNPs. These include, but are not limited to, ligation based assays, cleavage based assays (mismatch and invasive cleavage such as Invader™), single base extension methods (see WO 92/15712, EP 0 371 437 B1, EP 0317 074 B1; Pastinen et al., Genome Res. 7:606–614 (1997); Syvanen, Clinica Chimica Acta 226:225–236 (1994); and WO 91/13075), and competitive probe analysis (e.g. competitive sequencing by hybridization; see below).

Oligonucleotide ligation amplification ("OLA", which is referred as the ligation chain reaction (LCR) when two-stranded reactions) involves the ligation of two smaller probes into a single long probe, using the target sequence as the template. See generally U.S. Pat. Nos. 5,185,243, 5,679,524 and 5,573,907; EP 0 320 308 B1; EP 0 336 731 B1; EP 0 439 182 B1; WO 90/01069; WO 89/12696; WO 97/31256 and WO 89/09835, all of which are incorporated by reference.

Invasive cleavage technology is based on structure-specific nucleases that cleave nucleic acids in a site-specific manner. Two probes are used: an "invader" probe and a "signalling" probe, that adjacently hybridize to a target sequence with a non-complementary overlap. The enzyme cleaves at the overlap due to its recognition of the "tail", and releases the "tail" with a label. This can then be detected. The Invader™ technology is described in U.S. Pat. Nos. 5,846,717; 5,614,402; 5,719,028; 5,541,311; and 5,843,669, all of which are hereby incorporated by reference.

An additional technique utilizes sequencing by hybridization. For example, sequencing by hybridization has been described (Drmanac et al., Genomics 4:114 (1989); Koster et al., Nature Biotechnology 14:1123 (1996); U.S. Pat. Nos. 5,525,464; 5,202,231 and 5,695,940, among others, all of which are hereby expressly incorporated by reference in their entirety).

WO99/18434, WO99/67641and WO98/40726; WO98/50782; U.S. Ser. Nos. 09/287,573, 09/316,154(US 20020051971), 60/119,323; and U.S.P.N.s 6,327,410, 6,429,027, and 6,544,732; all of which are expressly incorporated by reference, describe novel compositions utilizing substrates with microsphere arrays, which allow for novel detection methods of nucleic acid hybridization.

However, none of the current methods allow the rapid, facile and inexpensive analysis of a variety of patient samples in parallel. Accordingly, it is an object of the present invention to provide methods and compositions for such determinations.

SUMMARY OF THE INVENTION

Accordingly, the present invention provides an array composition comprising a substrate with a surface comprising discrete sites, and a population of microspheres comprising at least a first and a second subpopulation, wherein the microspheres of each subpopulation each comprise a plurality of target analytes, wherein the microspheres are distributed on said surface.

In addition, the invention provides a method comprising providing an array composition comprising a substrate with a surface comprising discrete sites and a population of microspheres comprising at least a first and a second subpopulation, wherein the microspheres of each subpopulation each comprise a plurality of target analytes, wherein the microspheres are distributed on the surface. The method further includes contacting the array composition with a first set of readout probes and detecting the presence of a first target analyte.

In addition the method includes a method of genotyping comprising providing an array composition comprising a substrate with a surface comprising discrete sites and a population of microspheres comprising at least a first and a second subpopulation, wherein the microspheres of each subpopulation each comprise at least first and second target analytes attached to said microspheres with first and second attachment moieties, respectively, wherein the microspheres are distributed on the surface, contacting the array composition with a first set of extension probes that hybridize with at least the first target sequence adjacent to a first detection position to form an extension complex. The method further includes contacting the extension complex with a composition comprising at least a first nucleotide and polymerase wherein the polymerase extends a first extension probe with the first nucleotide when the first nucleotide is complementary to the first detection position of the first target sequence and detecting the presence of the first nucleotide.

In addition the invention provides a method of determining the identification of a nucleotide at a detection position in at least a first target sequence comprising providing an array composition comprising a substrate with a surface comprising discrete sites and a population of microspheres comprising at least a first and a second subpopulation, wherein the microspheres of each subpopulation each comprise a plurality of target sequences. The method further includes forming a first hybridization complex between the first target sequence and at least a first readout probe; and determining the nucleotide at the detection position.

DETAILED DESCRIPTION OF THE INVENTION

Figure 1:
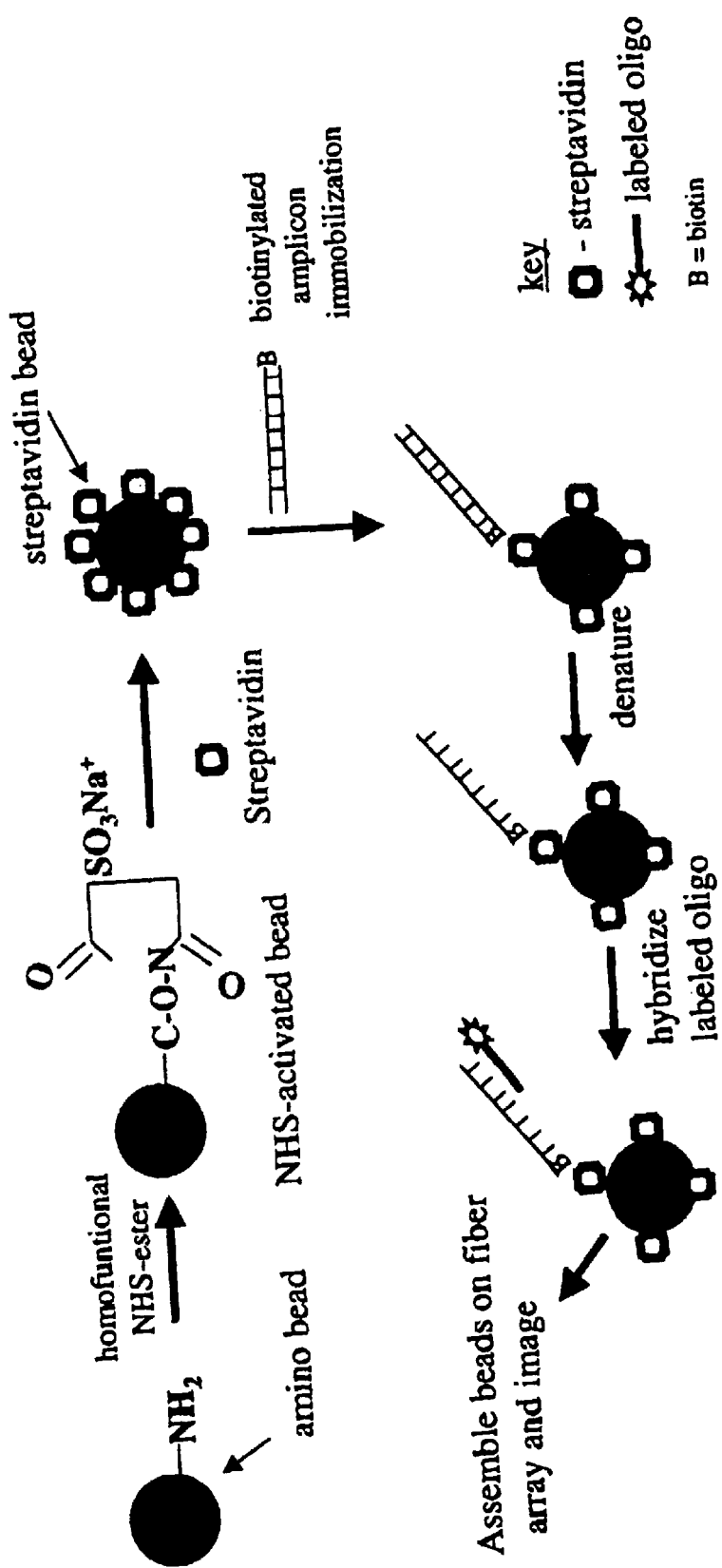
FIG. 1 depicts a flow chart for immobilizing target analytes to streptavidin coated beads.

The present invention capitalizes on previous work directed to the use of arrays of microspheres or beads that carry different chemical functionalities (such as proteins and nucleic acids) and are distributed on a substrate comprising a patterned surface of discrete sites that can associate the individual microspheres. In these arrays, the beads are generally put onto the substrate randomly and thus require the use of encoding/decoding systems that can correlate the location of the bead with the chemical functionality. This can be done in a variety of ways; see for example WO99/18434; and U.S. Ser. Nos. 09/473,904; 60/119,323; 60/160, 027; 60/161,148; 60/135,053; 09/425,633; 60/160,917; 09/287,573; and 60/151,668; and U.S.P.N.s 6,544,732; 6,327,410; 6,266,459.

In the present invention, samples from different patients are individually prepared using standard techniques as outlined below. The preparation can include the incorporation of moieties (termed "attachment moieties") to allow the attachment of the sample components to the beads, or the amplification or enrichment of individual sample components (i.e. different proteins or different nucleic acid sequences). After sample preparation, the mixture of patient sample components is attached to microspheres, such that multiple sample components from one patient are attached to a single bead. As outlined below, the beads can be encoded in a variety of ways. Then beads from different patients are combined and added to a substrate to create an array. The array can be "decoded", that is, a correlation of the location of an individual site on the array with the bead or candidate agent at that particular site can be made. As outlined below, this can be done either before, during or after the assay. The assay comprises the detection of individual sample components as outlined below. In this way, the parallel analysis of a large number of sample components from a large number of patients can be done. Alternatively, each bead can contain a different plurality of sample components from a single patient, thus allowing a large number of assays on a single patient sample.

While generally described for human patients, the compositions and methods of the invention find use in detection of sample components from a variety of sources. That is, the "target source" or source of target sample need not be limited to patients or even to humans. Indeed the method finds use in detection of sample components from any number of sources including, plants, animals, and microorganisms such as bacteria and viruses. In a preferred embodiment the source is a mammal including humans, domestic and farm animals, and zoo, sports, or pet animals, such as dogs, cats, cattle, horses, sheep, pigs, goats, rabbits, etc. Preferably, the mammal is human. In addition, the source is a cell type, including prokaryotic or eukaryotic cells. Suitable prokaryotic cells include, but are not limited to, bacteria such as *E. coli*, Bacillus species, and the extremophile bacteria such as thermophiles, etc. Preferably, the procaryotic target cells are recombination competent. Suitable eukaryotic cells include, but are not limited to, fungi such as yeast and filamentous fungi, including species of Aspergillus, Trichoderma, and Neurospora; plant cells including those of corn, sorghum, tobacco, canola, soybean, cotton, tomato, potato, alfalfa, sunflower, etc.; and animal cells, including fish, birds and mammals. Suitable fish cells include, but are not limited to, those from species of salmon, trout, tulapia, tuna, carp, flounder, halibut, swordfish, cod and zebrafish. Suitable bird cells include, but are not limited to, those of chickens, ducks, quail, pheasants and turkeys, and other jungle fowl or game birds. Suitable mammalian cells include, but are not limited to, cells from horses, cattle, buffalo, deer, sheep, rabbits, rodents such as mice, rats, hamsters, gerbils, and guinea pigs, minks, goats, pigs, primates, marsupials, marine mammals including dolphins and whales, as well as cell lines, such as human cell lines of any tissue or stem cell type, and stem cells, including pluripotent and non-pluripotent, and non-human zygotes.

In addition suitable cell types include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes.

Suitable cells also include known research cells, including, but not limited to, Jurkat T cells, NIH3T3 cells, CHO, Cos, etc. See the ATCC cell line catalog, hereby expressly incorporated by reference.

In a preferred embodiment, the present invention provides methods and compositions for the detection of patient sample components in samples. As will be appreciated by those in the art, the sample solution may comprise any number of things, including, but not limited to, bodily fluids (including, but not limited to, blood, urine, serum, lymph, saliva, anal and vaginal secretions, perspiration and semen, of virtually any organism, with mammalian samples being preferred and human samples being particularly preferred); environmental samples (including, but not limited to, air, agricultural, water and soil samples); biological warfare agent samples; research samples (i.e. in the case of nucleic acids, the sample may be the products of an amplification reaction, including both target and signal amplification as is generally described in U.S. Ser. No. 60/161,148; hereby incorporated by reference) such as PCR amplification reaction); purified samples, such as purified genomic DNA, RNA, proteins, etc.; raw samples (bacteria, virus, genomic DNA, etc.; As will be appreciated by those in the art, virtually any experimental manipulation may have been done on the sample. Preferred samples are from one or more human samples.

The present invention is directed to the detection of patient sample components or target analytes. By "patient sample components" or "target analytes" or grammatical equivalents herein is meant any molecule in the sample which is to be detected, with proteins and nucleic acids being preferred, and nucleic acids being particularly preferred.

By "nucleic acid" or "oligonucleotide" or grammatical equivalents herein means at least two nucleotides covalently linked together. A nucleic acid of the present invention will generally contain phosphodiester bonds, although in some cases, as outlined below (for example for readout probes, identifier binding ligands, etc), nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference).

Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp169176). Several nucleic acid analogs are described in Rawls. C & E News Jun. 2, 1997 page 35. All of these references are hereby expressly incorporated by reference. These modifications of the ribose-phosphate backbone may be done to facilitate the addition of labels, alter the hybridization properties of the nucleic acids, or to increase the stability and half-life of such molecules in physiological environments.

As will be appreciated by those in the art, all of these nucleic acid analogs may find use in the present invention. In addition, mixtures of naturally occurring nucleic acids and analogs can be made. Alternatively, mixtures of different nucleic acid analogs, and mixtures of naturally occuring nucleic acids and analogs may be made.

Particularly preferred are peptide nucleic acids (PNA) which includes peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature (Tm) for mismatched versus perfectly matched basepairs. DNA and RNA typically exhibit a 2–4° C. drop in Tm for an internal mismatch. With the non-ionic PNA backbone, the drop is closer to 7–9° C. This allows for better detection of mismatches. Similarly, due to their non-ionic nature, hybridization of the bases attached to these backbones is relatively insensitive to salt concentration. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribonucleotides, and any combination of bases, including uracil, adenine, thymine, cytosine, guanine, inosine, xathanine hypoxathanine, isocytosine, isoguanine, etc. A preferred embodiment utilizes isocytosine and isoguanine in nucleic acids designed to be complementary to other probes, rather than target sequences, as this reduces non-specific hybridization, as is generally described in U.S. Pat. No. 5,681,702. As used herein, the term "nucleoside" includes nucleotides as well as nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

In a preferred embodiment, the compositions and methods of the invention are directed to the detection of target sequences as the target analytes. The term "target sequence"

or "target nucleic acid" or grammatical equivalents herein means a nucleic acid sequence on a single strand of nucleic acid. The target sequence may be a portion of a gene, a regulatory sequence, genomic DNA, cDNA, RNA including mRNA and rRNA, or others. As is outlined herein, the target sequence may be a target sequence from a sample that has been amplified. It may be any length, with the understanding that longer sequences are more specific. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others. As is outlined more fully below, readout probes are made to hybridize to target sequences to determine the presence or absence of the target sequence in a sample. Generally speaking, this term will be understood by those skilled in the art. The target sequence may also be comprised of different target domains. The target domains may be adjacent or separated as indicated.

Unless specified, the terms "first" and "second" are not meant to confer an orientation of the sequences with respect to the 5'-3'orientation of the target sequence. For example, assuming a 5'-3' orientation of the complementary target sequence, the first target domain may be located either 5' to the second domain, or 3' to the second domain.

The target analytes are grouped into sets that are placed on sites on the array. For example, when bead arrays are used to detect target sequences, each bead subpopulation comprises a particular set of target sequences. As outlined herein, each set may be from a different patient, or each set may be from one patient, with the sets being different. That is, in one embodiment, each subpopulation of beads includes a set of target sequences from a different patient. In an alternative embodiment, a subpopulation of beads includes a different set of target sequences from a single patient. By "set" means at least two or more different target sequences.

The present invention provides array compositions comprising substrates with surfaces comprising discrete sites. By "array" or "biochip" herein is meant a plurality of target analyte sets in an array format; the size of the array will depend on the composition and end use of the array. That is, each site on the array comprises a set of target analytes. Nucleic acids arrays are known in the art, and can be classified in a number of ways; both ordered arrays (e.g. the ability to resolve chemistries at discrete sites), and random arrays are included. Ordered arrays include, but are not limited to, those made using photolithography techniques (Affymetrix GeneChip™), spotting techniques (Synteni and others), printing techniques (Hewlett Packard and Rosetta), three dimensional "gel pad" arrays, etc. A preferred embodiment utilizes microspheres on a variety of substrates including fiber optic bundles, as are outlined in WO99/18434, WO99/68641, WO98/40726, WO98/50782; U.S.S.N.s 09/287,573, 09/316,154(US 20020051971), 60/119,323; and U.S.P.N.s 6,327,410, 6,429,027, and 6,544,732, all of which are expressly incorporated by reference. While much of the discussion below is directed to the use of microsphere arrays on substrates such as fiber optic bundles, any array format of nucleic acids on solid supports may be utilized.

Arrays containing from about 2 different target analyte sets (i.e. 2 different beads, with each bead comprising a particular set of target analytes) to many millions can be made, with very large arrays being possible. Generally, the array will comprise from two to as many as a billion or more, depending on the size of the beads and the substrate, as well as the end use of the array, thus very high density, high density, moderate density, low density and very low density arrays may be made. Preferred ranges for very high density arrays are from about 10,000,000 to about 2,000,000,000, with from about 100,000,000 to about 1,000,000,000 being preferred (all numbers being in square cm). High density arrays range about 100,000 to about 10,000,000, with from about 1,000,000 to about 5,000,000 being particularly preferred. Moderate density arrays range from about 10,000 to about 100,000 being particularly preferred, and from about 20,000 to about 50,000 being especially preferred. Low density arrays are generally less than 10,000, with from about 1,000 to about 5,000 being preferred. Very low density arrays are less than 1,000, with from about 10 to about 1000 being preferred, and from about 100 to about 500 being particularly preferred. In some embodiments, the compositions of the invention may not be in array format; that is, for some embodiments, compositions comprising a single target analyte set may be made as well. In addition, in some arrays, multiple substrates may be used, either of different or identical compositions. Thus for example, large arrays may comprise a plurality of smaller substrates.

In addition, one advantage of the present compositions is that particularly through the use of fiber optic technology, extremely high density arrays can be made. Thus for example, because beads of 200 pm or less (with beads of 200 nm possible) can be used, and very small fibers are known, it is possible to have as many as 40,000 or more (in some instances, 1 million) different elements (e.g. fibers and beads) in a 1 mm$^2$ fiber optic bundle, with densities of greater than 25,000,000 individual beads and fibers (again, in some instances as many as 50–100 million) per 0.5 cm$^2$ obtainable (4 million per square cm for 5μ center-to-center and 100 million per square cm for 1μ center-to-center).

By "substrate" or "solid support" or other grammatical equivalents herein is meant any material that can be modified to contain discrete individual sites appropriate for the attachment or association of beads and is amenable to at least one detection method. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon and modified silicon, carbon, metals, inorganic glasses, plastics, optical fiber bundles, and a variety of other polymers. In general, the substrates allow optical detection and do not themselves appreciably fluoresce.

Generally the substrate is flat (planar), although as will be appreciated by those in the art, other configurations of substrates may be used as well; for example, three dimensional configurations can be used, for example by embedding the beads in a porous block of plastic that allows sample access to the beads and using a confocal microscope for detection. Similarly, the beads may be placed on the inside surface of a tube, for flow-through sample analysis to minimize sample volume. Preferred substrates include optical fiber bundles as discussed below, and flat planar substrates such as glass, polystyrene and other plastics and acrylics.

In a preferred embodiment, the substrate is an optical fiber bundle or array, as is generally described in U.S. Ser. Nos. 08/944,850, 09/287,573 and U.S. Pat. No. 6,200,737; WO98/40726, and PCT US98/09163, and WO 99/18434, all of which are expressly incorporated herein by reference. Preferred embodiments utilize preformed unitary fiber optic arrays. By "preformed unitary fiber optic array" herein is meant an array of discrete individual fiber optic strands that are co-axially disposed and joined along their lengths. The fiber strands are generally individually clad. However, one thing that distinguished a preformed unitary array from other fiber optic formats is that the fibers are not individually physically manipulatable; that is, one strand generally cannot be physically separated at any point along its length from another fiber strand.

Generally, the array of array compositions of the invention can be configured in several ways; see for example U.S. Ser. Nos. 09/473,904, 09/606,369 and WO 00/39587, all of which are hereby expressly incorporated by reference. In a preferred embodiment, as is more fully outlined below, a "one component" system is used. That is, a first substrate comprising a plurality of assay locations (sometimes also referred to herein as "assay wells"), such as a microtiter plate, is configured such that each assay location contains an individual array. That is, the assay location and the array location are the same. For example, the plastic material of the microtiter plate can be formed to contain a plurality of "bead wells" in the bottom of each of the assay wells. Beads containing the capture probes of the invention can then be loaded into the bead wells in each assay location as is more fully described below.

In an alternative embodiment, the substrate is a microscope slide or formed with the dimensions of a microscope slide. An advantage of using substrates of this size is that existing instrumentation, i.e. detectors can be used to analyze signals on the substrate. That is, existing scanning-based instrumentation including, but not limited to, that sold by General Scanning, Molecular Dynamics, Gene Machine, Genetic Microsystems, Vysis, Axon and Hewlett-Packard can be used to analyze arrays of the present invention.

Alternatively, a "two component" system can be used. In this embodiment, the individual arrays are formed on a second substrate, which then can be fitted or "dipped" into the first microtiter plate substrate. A preferred embodiment utilizes fiber optic bundles as the individual arrays, generally with "bead wells" etched into one surface of each individual fiber, such that the beads containing the capture probes are loaded onto the end of the fiber optic bundle. The composite array thus comprises a number of individual arrays that are configured to fit within the wells of a microtiter plate.

By "composite array" or "combination array" or grammatical equivalents herein is meant a plurality of individual arrays, as outlined above. Generally the number of individual arrays is set by the size of the microtiter plate used; thus, 96 well, 384 well and 1536 well microtiter plates utilize composite arrays comprising 96,384 and 1536 individual arrays, although as will be appreciated by those in the art, not each microtiter well need contain an individual array. It should be noted that the composite arrays can comprise individual arrays that are identical, similar or different. That is, in some embodiments, it may be desirable to do the same 2,000 assays on 96 different samples; alternatively, doing 192,000 experiments on the same sample (i.e. the same sample in each of the 96 wells) may be desirable. Alternatively, each row or column of the composite array could be the same, for redundancy/quality control. As will be appreciated by those in the art, there are a variety of ways to configure the system. In addition, the random nature of the arrays may mean that the same population of beads may be added to two different surfaces, resulting in substantially similar but perhaps not identical arrays.

At least one surface of the substrate is modified to contain discrete, individual sites for later association of microspheres. These sites may comprise physically altered sites, i.e. physical configurations such as wells or small depressions in the substrate that can retain the beads, such that a microsphere can rest in the well, or the use of other forces (magnetic or compressive), or chemically altered or active sites, such as chemically functionalized sites, electrostatically altered sites, hydrophobically/hydrophilically functionalized sites, spots of adhesive, etc.

The sites may be a pattern, i.e. a regular design or configuration, or randomly distributed. A preferred embodiment utilizes a regular pattern of sites such that the sites may be addressed in the X-Y coordinate plane. "Pattern" in this sense includes a repeating unit cell, preferably one that allows a high density of beads on the substrate. However, it should be noted that these sites may not be discrete sites. That is, it is possible to use a uniform surface of adhesive or chemical functionalities, for example, that allows the attachment of beads at any position. That is, the surface of the substrate is modified to allow attachment of the microspheres at individual sites, whether or not those sites are contiguous or non-contiguous with other sites. Thus, the surface of the substrate may be modified such that discrete sites are formed that can only have a single associated bead, or alternatively, the surface of the substrate is modified and beads may go down anywhere, but they end up at discrete sites.

In a preferred embodiment, the surface of the substrate is modified to contain wells, i.e. depressions in the surface of the substrate. This may be done as is generally known in the art using a variety of techniques, including, but not limited to, photolithography, stamping techniques, molding techniques and microetching techniques. As will be appreciated by those in the art, the technique used will depend on the composition and shape of the substrate.

In a preferred embodiment, physical alterations are made in a surface of the substrate to produce the sites. In a preferred embodiment, the substrate is a fiber optic bundle and the surface of the substrate is a terminal end of the fiber bundle, as is generally described in Ser. Nos. 6,023,540 and 6,327,410, both of which are hereby expressly incorporated by reference. In this embodiment, wells are made in a terminal or distal end of a fiber optic bundle comprising individual fibers. In this embodiment, the cores of the individual fibers are etched, with respect to the cladding, such that small wells or depressions are formed at one end of the fibers. The required depth of the wells will depend on the size of the beads to be added to the wells.

Generally in this embodiment, the microspheres are non-covalently associated in the wells, although the wells may additionally be chemically functionalized as is generally described below, cross-linking agents may be used, or a physical barrier may be used, i.e. a film or membrane over the beads.

In a preferred embodiment, the surface of the substrate is modified to contain chemically modified sites, that can be used to attach, either covalently or non-covalently, the microspheres of the invention to the discrete sites or locations on the substrate. "Chemically modified sites" in this context includes, but is not limited to, the addition of a pattern of chemical functional groups including amino groups, carboxy groups, oxo groups and thiol groups, that can be used to covalently attach microspheres, which generally also contain corresponding reactive functional groups; the addition of a pattern of adhesive that can be used to bind the microspheres (either by prior chemical functionalization for the addition of the adhesive or direct addition of the adhesive); the addition of a pattern of charged groups (similar to the chemical functionalities) for the electrostatic attachment of the microspheres, i.e. when the microspheres comprise charged groups opposite to the sites; the addition of a pattern of chemical functional groups that renders the sites differentially hydrophobic or hydrophilic, such that the addition of similarly hydrophobic or hydrophilic microspheres under suitable experimental conditions will result in association of the microspheres to the sites on the basis of hydroaffinity. For example, the use of hydrophobic sites with hydrophobic beads, in an aqueous system, drives the association of the beads preferentially onto the sites. As outlined above, "pattern" in this sense includes the use of a uniform treatment of the surface to allow attachment of the beads at discrete sites, as well as treatment of the surface resulting in discrete sites. As will be appreciated by those in the art, this may be accomplished in a variety of ways.

In a preferred embodiment, the compositions of the invention further comprise a population of microspheres. By "population" herein is meant a plurality of beads as outlined above for arrays. Within the population are separate subpopulations, which can be a single microsphere or multiple identical microspheres. That is, in some embodiments, as is more fully outlined below, the array may contain only a single bead for each patient set; preferred embodiments utilize a plurality of beads of each type.

By "microspheres" or "beads" or "particles" or grammatical equivalents herein is meant small discrete particles. The composition of the beads will vary, depending on the class of target analyte, the method of attachment and the method of synthesis. Suitable bead compositions include those used in peptide, nucleic acid and organic moiety synthesis, including, but not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, crosslinked micelles and Teflon may all be used. "*Microsphere Detection Guide*" from Bangs Laboratories, Fishers Ind. is a helpful guide.

The beads need not be spherical; irregular particles may be used. In addition, the beads may be porous, thus increasing the surface area of the bead available for either target analyte attachment or tag attachment. The bead sizes range from nanometers, i.e. 100 nm, to millimeters, i.e. 1 mm, with beads from about 0.2 micron to about 200 microns being preferred, and from about 0.5 to about 5 micron being particularly preferred, although in some embodiments smaller beads may be used.

It should be noted that a key component of the invention is the use of a substrate/bead pairing that allows the association or attachment of the beads at discrete sites on the surface of the substrate, such that the beads do not move during the course of the assay.

Each microsphere comprises a set of target analytes, although as will be appreciated by those in the art, there may be some microspheres which do not contain target analytes, depending on the synthetic methods.

The size of the target analyte set will vary with the assay being done and the desired information. For example, from 2 to 100,000 different target analytes may make up a set. That is, when beads are used, each bead can comprise from 2 to 100,000 different target analytes, with from 10 to 10,000 being particularly preferred and from 100 to 1000 being especially preferred.

Attachment of the target analytes may be done in a variety of ways, as will be appreciated by those in the art. For nucleic acids, preferred methods include, but are not limited to, chemical or affinity capture (for example, including the incorporation of derivatized nucleotides such as AminoLink or biotinylated nucleotides that can then be used to attach the nucleic acid to a surface, as well as affinity capture by hybridization), phenylboronic acid (PBA) conjugation, salicylhydroxamic acid (SHA) conjugation, covalent immobilization through amide formation, cross-linking, and electrostatic attachment, etc. Alternatively, the target analyte nucleic acids can be adsorbed to functionalized beads such as amino-beads, i.e. amino-modified beads. For protein target analytes, generally binding partners such as antibodies are used; a first antibody is attached to the beads using well known chemistries, and then the protein analytes are added.

In a preferred embodiment, when the target analytes are nucleic acids, the target sequences are prepared from the sample to include an attachment moiety for subsequent attachment to the beads (or surface, for non-bead based arrays). This can be done in several ways. In a preferred embodiment, this is done by incorporating the attachment linker into a nucleotide, for subsequent incorporation into the target sequence during an enzymatic amplification. Alternatively, and preferably, the attachment linker may be part of a primer used in the amplification reaction, such that the attachment linker is either at the 3' or 5' end of the target sequence.

As will be appreciated by those in the art, the target sequences on the surface of the array (e.g. attached to the microspheres) may be attached in either orientation, either such that they have a free 3' end or a free 5' end; in some embodiments, the probes can be attached at one ore more internal positions, or at both ends.

In a preferred embodiment, affinity capture is used to attach the nucleic acids to the beads. For example, nucleic acids can be derivatized, for example with one member of a binding pair, and the beads derivatized with the other member of a binding pair. Suitable binding pairs are as described herein for IBL/DBL pairs. For example, the nucleic acids may be biotinylated (for example using enzymatic incorporate of biotinylated nucleotides, for by photoactivated cross-linking of biotin). Biotinylated nucleic acids can then be captured on streptavidin-coated beads, as is known in the art. Similarly, other hapten-receptor combinations can be used, such as digoxigenin and anti-digoxigenin antibodies. Alternatively, chemical groups can be added in the form of derivatized nucleotides, that can them be used to add the nucleic acid to the surface.

Preferred attachments are covalent, although even relatively weak interactions (i.e. non-covalent) can be sufficient to attach a nucleic acid to a surface, if there are multiple sites of attachment per each nucleic acid. Thus, for example, electrostatic interactions can be used for attachment, for example by having beads carrying the opposite charge to the target analyte.

Similarly, affinity capture utilizing hybridization can be used to attach nucleic acids to beads. For example, as is known in the art, polyA+RNA is routinely captured by hybridization to oligo-dT beads; this may include oligo-dT capture followed by a cross-linking step, such as psoralen crosslinking). If the nucleic acids of interest do not contain a polyA tract, one can be attached by polymerization with terminal transferase, or via ligation of an oligoA linker, as is known in the art.

Alternatively, chemical crosslinking may be done, for example by photoactivated crosslinking of thymidine to reactive groups, as is known in the art.

The incorporation of specific attachment linkers or chemistries into the target sequence can be used for attachment to a site. The functionalization of solid support surfaces such as certain polymers with chemically reactive groups such as thiols, amines, carboxyls, etc. is generally known in the art. Accordingly, "blank" microspheres may be used that have surface chemistries that facilitate the attachment of the desired functionality by the user. Some examples of these surface chemistries for blank microspheres include, but are not limited to, amino groups including aliphatic and aromatic amines, carboxylic acids, aldehydes, amides, chloromethyl groups, hydrazide, hydroxyl groups, sulfonates and sulfates.

In a preferred embodiment, linkers are used to attach the target analytes to the beads, to allow both good attachment, sufficient flexibility to allow good interaction with the probes, described below, and to avoid undesirable binding reactions.

It should be noted that the method of attachment of the set of target analytes to the bead results in a known combination of target analytes to a particular bead. That is, for example, a multiplexing PCR reaction can be done using known primers, or several PCR reactions can be done, that result in specific amplification of a set of sequences in a pool.

There are two general ways to attach the target sets to the site of the array. As outlined herein, one way is to have the amplification primers comprise an attachment moiety that can be used to attach to a site on the array. Thus for example the use of biotinylated target sequences can allow the attachment of a target set to a streptavidin coated bead, or to a spot of streptavidin on an array surface (that can be spotted down using any variety of methods, as is known in the art). Alternatively, amplification primers comprising adapter sequences such as are described in U.S. Ser. Nos. 60/160, 917, 09/553,993 and 09/556,463, hereby incorporated by reference in their entirety, can be used to attach to a bead (or a spot on an array) comprising a capture probe substantially complementary to the adapter sequence. Thus, in one embodiment, all the amplification primers of a single patient sample can comprise a single unique adapter such that they all hybridize to a single spot (i.e. bead) of the array. This then is run in a "sandwich" type assay, where the array comprises a capture probe, hybridized to a first portion of the target sequence comprising the adapter sequence, and a readout probe as outlined herein hybridized to a second portion of the target sequence.

This pool is then added to a bead; thus, the set of target sequences is known for a bead subpopulation. In addition, although not discussed specifically herein, there are a wide variety of known methods for amplification of nucleic acids. Briefly, these techniques can be classified as either target amplification or signal amplification. Target amplification involves the amplification (i.e. replication) of the target sequence to be detected, resulting in a significant increase in the number of target molecules. Target amplification strategies include the polymerase chain reaction (PCR), strand displacement amplification (SDA), and nucleic acid sequence based amplification (NASBA). Alternatively, rather than amplify the target, alternate techniques use the target as a template to replicate a signalling probe, allowing a small number of target molecules to result in a large number of signalling probes, that then can be used as the target analyte. Signal amplification strategies include the ligase chain reaction (LCR), cycling probe technology (CPT), invasive cleavage techniques such as Invader™ technology, Q-Beta replicase (QβR) technology. See U.S. Ser. Nos. 60/161,148, 09/553,993 and 090/556,463, and U.S. Pat. No. 6,355,431; hereby expressly incorporated by reference in their entirety.

When microsphere arrays are used, an encoding/decoding system must be used. That is, since the beads are generally put onto the substrate randomly, there are several ways to correlate the set on the bead with its location, and generally includes: a) the use a decoding binding ligand (DBL), generally directly labeled, that binds to a unique identifier binding ligands (IBLs) attached to the beads; b) positional decoding, for example by either targeting the placement of beads (for example by using photoactivatible or photocleavable moieties to allow the selective addition of beads to particular locations), or by using either sub-bundles or selective loading of the sites, as are more fully outlined below; c) selective decoding, wherein only those beads that bind to a target are decoded; d) the use of optical signatures such as unique optical dyes for each subpopulation; or e) combinations of any of these. In some cases, as is more fully outlined below, this decoding may occur for all the beads, or only for those that contain a particular target analyte. Similarly, this may occur either prior to, during or after the assay.

Thus, in a preferred embodiment, the microspheres of the invention comprise optical signatures or optical codes. That is, as outlined in U.S. Pat. Nos. 6,023,540, 6,327,410, and U.S. Ser. Nos. 6,266,459(all of which are expressly incorporated herein by reference), each subpopulation of microspheres can comprise a unique optical signature or optical tag that is used to identify the target analyte set of that subpopulation of microspheres; that is, decoding utilizes optical properties of the beads such that a bead comprising the unique optical signature may be distinguished from beads at other locations with different optical signatures. Thus the previous work assigned each capture probe a unique optical signature such that any microspheres comprising that capture probe are identifiable on the basis of the signature. These optical signatures comprised dyes, usually chromophores or fluorophores, that were entrapped or attached to the beads themselves. Diversity of optical signatures utilized different fluorochromes, different ratios of mixtures of fluorochromes, and different concentrations (intensities) of fluorochromes.

Alternatively, or in addition to, the microspheres can further comprise an identifier binding ligand. That is, in this embodiment, "decoding" does not rely on the use of optical signatures, but rather on the use of decoding binding ligands that are added during a decoding step. The decoding binding ligands will bind to a distinct identifier binding ligand partner that is placed on the beads. The decoding binding ligands are either directly or indirectly labeled, and thus decoding occurs by detecting the presence of the label. By using pools of decoding binding ligands in a sequential fashion, it is possible to greatly minimize the number of required decoding steps.

It should be noted that in some cases, the identifier binding ligand is one of the target analytes in the set. However, this is generally not preferred. Rather, preferred embodiments utilize a unique IBL for each bead.

By "identifier binding ligands" or "IBLs" herein is meant a compound that will specifically bind a corresponding decoder binding ligand (DBL) to facilitate the elucidation of the identity of the set attached to the bead. That is, the IBL and the corresponding DBL form a binding partner pair. By "specifically bind" herein is meant that the IBL binds its DBL with specificity sufficient to differentiate between the corresponding DBL and other DBLs (that is, DBLs for other IBLs), or other components or contaminants of the system. The binding should be sufficient to remain bound under the conditions of the decoding step, including wash steps to remove non-specific binding. In some embodiments, for example when the IBLs and corresponding DBLs are proteins or nucleic acids, the dissociation constants of the IBL to its DBL will be less than about $10^{-4}$–$10^{-6}$ $M^{-1}$, with less than about $10^{-5}$ to $10^{-9}$ $M^{-1}$ being preferred and less than about $10^{-7}$–$10^{-9}$ $M^{-1}$ being particularly preferred.

IBL-DBL binding pairs are known or can be readily found using known techniques. For example, when the IBL is a protein, the DBLs include proteins (particularly including antibodies or fragments thereof (FAbs, etc.)) or small molecules, or vice versa (the IBL is an antibody and the DBL is a protein). Metal ion-metal ion ligands or chelators pairs are also useful. Antigen-antibody pairs, enzymes and substrates or inhibitors, other protein—protein interacting pairs, receptor-ligands, complementary nucleic acids, and carbohydrates and their binding partners are also suitable binding pairs. Nucleic acid—nucleic acid binding proteins pairs are also useful. Similarly, as is generally described in U.S. Pat. Nos. 5,270,163, 5,475,096, 5,567,588, 5,595,877, 5,637,459, 5,683,867,5,705,337, and related patents, hereby incorporated by reference, nucleic acid "aptamers" can be developed for binding to virtually any target; such an aptamer-target pair can be used as the IBL-DBL pair. Similarly, there is a wide body of literature relating to the development of binding pairs based on combinatorial chemistry methods.

In a preferred embodiment, the IBL is a molecule whose color or luminescence properties change in the presence of a selectively-binding DBL. For example, the IBL may be a fluorescent pH indicator whose emission intensity changes with pH. Similarly, the IBL may be a fluorescent ion indicator, whose emission properties change with ion concentration.

In a preferred embodiment, the IBL is a protein, particularly an enzyme, that is conjugated to a bead.

One advantage of using proteins/enzymes as IBLs is that many proteins and enzymes are commercially available in relatively pure preparations. Proteins contain many suitable functional groups for attachment to beads. Moreover, the identity of many small molecules including substrates that bind the proteins/enzymes are known. Such small molecules serve as the DBL. In addition, the small molecule can serve as the IBL and the enzyme as the DBL. As will be appreciated by those in the art, combinations of enzymes and small molecules can be used as well, or multiple enzymes and small molecules. Another potential advantage relates to the purification of the labeled proteins. If one conjugates a fluorophore to a recrystallizable protein, then the unlabeled protein can be removed from labeled protein by use of crystallization. By filtering off the crystalline solid, the labeled protein will be concentrated in the filtrate.

In an alternative embodiment, antigen-antibody pairs are used as DBL-IBL combinations. In one embodiment antibodies are conjugated to different labels, defined below, that are then used to decode antigen-labeled beads.

Alternatively, the IBL is a molecule whose color or luminescence properties change in the presence of various solvents. For example, the IBL may be a fluorescent molecule such as an ethidium salt whose fluorescence intensity increases in hydrophobic environments. Similarly, the IBL may be a derivative of fluorescein whose color changes between aqueous and nonpolar solvents.

In one embodiment, the DBL may be attached to a bead, i.e. a "decoder bead", that may carry a label such as a fluorophore.

In a preferred embodiment, the IBL-DBL pair comprise substantially complementary single-stranded nucleic acids. In this embodiment, the binding ligands can be referred to as "identifier probes" and "decoder probes". Generally, the identifier and decoder probes range from about 4 basepairs in length to about 1000, with from about 6 to about 100 being preferred, and from about 8 to about 40 being particularly preferred. What is important is that the probes are long enough to be specific, i.e. to distinguish between different IBL-DBL pairs, yet short enough to allow both a) dissociation, if necessary, under suitable experimental conditions, and b) efficient hybridization.

In a preferred embodiment, as is more fully outlined below, the IBLs do not bind to DBLs. Rather, the IBLs are used as identifier moieties ("IMs") that are identified directly, for example through the use of mass spectroscopy.

In a preferred embodiment, the present invention does not rely solely on the use of optical properties to decode the arrays. However, as will be appreciated by those in the art, it is possible in some embodiments to utilize optical signatures as an additional coding method, in conjunction with the present system. Thus, for example, as is more fully outlined below, the size of the array may be effectively increased while using a single set of decoding moieties in several ways, one of which is the use of optical signatures on some beads. Thus, for example, using one "set" of decoding molecules, the use of two populations of beads, one with an optical signature and one without, allows the effective doubling of the array size. The use of multiple optical signatures similarly increases the possible size of the array.

In a preferred embodiment, each subpopulation of beads comprises a plurality of different IBLs. By using a plurality of different IBLs to encode each target set, the number of possible unique codes is substantially increased. That is, by using one unique IBL per bead, the size of the array will be the number of unique IBLs (assuming no "reuse" occurs, as outlined below). However, by using a plurality of different IBLs per bead, n, the size of the array can be increased to $2^n$, when the presence or absence of each IBL is used as the indicator. For example, the assignment of 10 IBLs per bead generates a 10 bit binary code, where each bit can be designated as "1" (IBL is present) or "0" (IBL is absent). A 10 bit binary code has $2^{10}$ possible variants However, as is more fully discussed below, the size of the array may be further increased if another parameter is included such as concentration or intensity; thus for example, if two different concentrations of the IBL are used, then the array size increases as $3^n$. Thus, in this embodiment, each individual analyte set in the array is assigned a combination of IBLs, which can be added to the beads prior to or after the addition of the target analytes.

Alternatively, the combination of different IBLs can be used to elucidate the sequence of the nucleic acid. Thus, for example, using two different IBLs (IBL1 and IBL2), the first position of a nucleic acid can be elucidated: for example, adenosine can be represented by the presence of both IBL1 and IBL2; thymidine can be represented by the presence of IBL1 but not IBL2, cytosine can be represented by the presence of IBL2 but not IBL1, and guanosine can be represented by the absence of both. The second position of the nucleic acid can be done in a similar manner using IBL3 and IBL4; thus, the presence of IBL1, IBL2, IBL3 and IBL4 gives a sequence of AA; IBL1, IBL2, and IBL3 shows the sequence AT; IBL1, IBL3 and IBL4 gives the sequence TA, etc. The third position utilizes IBL5 and IBL6, etc. In this way, the use of 20 different identifiers can yield a unique code for every possible 10-mer.

In this way, a sort of "bar code" for each sequence can be constructed; the presence or absence of each distinct IBL will allow the identification of each target set.

In addition, the use of different concentrations or densities of IBLs allows a "reuse" of sorts. If, for example, the bead comprising a first agent has a 1× concentration of IBL, and a second bead comprising a second agent has a 10× concentration of IBL, using saturating concentrations of the corresponding labelled DBL allows the user to distinguish between the two beads. Decoding methods and compositions are outlined in more detail in U.S. Ser. Nos. 09/189,543, 09/344,526, 60/235,531 and 09/748,706 and WO 99/67641, all of which are expressly incorporated herein by reference.

Once the microspheres comprising the target analyte sets are generated, they are added to the substrate to form an array. It should be noted that while most of the methods described herein add the beads to the substrate prior to the assay, the order of making, using and decoding the array can vary. For example, the array can be made, decoded, and then the assay done. Alternatively, the array can be made, used in an assay, and then decoded; this may find particular use when only a few beads need be decoded. Alternatively, the beads can be added to the assay mixture, i.e. the sample containing the target sequences, prior to the addition of the beads to the substrate; after addition and assay, the array may be decoded. This is particularly preferred when the sample comprising the beads is agitated or mixed; this can increase the amount of readout probe bound to the beads per unit time, and thus (in the case of nucleic acid assays) increase the hybridization kinetics. This may find particular use in cases where the concentration of readout probe is low; generally, for low concentrations, long binding times must be used.

In general, the methods of making the arrays and of decoding the arrays is done to maximize the number of different target analyte sets that can be uniquely encoded. The compositions of the invention may be made in a variety of ways. In general, the arrays are made by adding a solution or slurry comprising the beads to a surface containing the sites for attachment of the beads. This may be done in a variety of buffers, including aqueous and organic solvents, and mixtures. The solvent can evaporate, and excess beads are removed.

In a preferred embodiment, when non-covalent methods are used to associate the beads with the array, a novel method of loading the beads onto the array is used. This method comprises exposing the array to a solution of particles and then applying energy, e.g. agitating or vibrating the mixture. This results in an array comprising more tightly associated particles, as the agitation is done with sufficient energy to cause weakly-associated beads to fall off (or out, in the case of wells). These sites are then available to bind a different bead. In this way, beads that exhibit a high affinity for the sites are selected. Arrays made in this way have two main advantages as compared to a more static loading: first of all, a higher percentage of the sites can be filled easily, and secondly, the arrays thus loaded show a substantial decrease in bead loss during assays. Thus, in a preferred embodiment, these methods are used to generate arrays that have at least about 50% of the sites filled, with at least about 75% being preferred, and at least about 90% being particularly preferred. Similarly, arrays generated in this manner preferably lose less than about 20% of the beads during an assay, with less than about 10% being preferred and less than about 5% being particularly preferred.

In this embodiment, the substrate comprising the surface with the discrete sites is immersed into a solution comprising the beads. The surface may comprise wells, as is described herein, or other types of sites on a patterned surface such that there is a differential affinity for the sites. This differential affinity results in a competitive process, such that particles that will associate more tightly are selected. Preferably, the entire surface to be "loaded" with beads is in fluid contact with the solution. This solution is generally a slurry ranging from about 10,000:1 beads:solution (vol:vol) to 1:1. Generally, the solution can comprise any number of reagents, including aqueous buffers, organic solvents, salts, other reagent components, etc. In addition, the solution preferably comprises an excess of beads; that is, there are more beads than sites on the array. Preferred embodiments utilize two-fold to billion-fold excess of beads.

The immersion can mimic the assay conditions; for example, if the array is to be "dipped" from above into a microtiter plate comprising readout probes, this configuration can be repeated for the loading, thus minimizing the beads that are likely to fall out due to gravity.

Once the surface has been immersed, the substrate, the solution, or both are subjected to a competitive process, whereby the particles with lower affinity can be disassociated from the substrate and replaced by particles exhibiting a higher affinity to the site. This competitive process is done by the introduction of energy, in the form of heat, sonication, stirring or mixing, vibrating or agitating the solution or substrate, or both.

A preferred embodiment utilizes agitation or vibration. In general, the amount of manipulation of the substrate is minimized to prevent damage to the array; thus, preferred embodiments utilize the agitation of the solution rather than the array, although either will work. As will be appreciated by those in the art, this agitation can take on any number of forms, with a preferred embodiment utilizing microtiter plates comprising bead solutions being agitated using microtiter plate shakers.

The agitation proceeds for a period of time sufficient to load the array to a desired fill. Depending on the size and concentration of the beads and the size of the array, this time may range from about 1 second to days, with from about 1 minute to about 24 hours being preferred.

In a preferred embodiment, the substrate is pressed into a mixture of dry beads (although slurries may be used as well), and then tapped to remove excess beads.

It should be noted that not all sites of an array may comprise a bead; that is, there may be some sites on the substrate surface which are empty. In addition, there may be some sites that contain more than one bead, although this is not preferred.

In some embodiments, for example when chemical attachment is done, it is possible to attach the beads in a non-random or ordered way. For example, using photoactivatible attachment linkers or photoactivatible adhesives or masks, selected sites on the array may be sequentially rendered suitable for attachment, such that defined populations of beads are laid down.

The arrays of the present invention are constructed such that information about the identity of the target set is built into the array, such that the random deposition of the beads on the sites can be "decoded" to allow identification of the target sets at all positions. This may be done in a variety of ways, and either before, during or after the use of the array to detect target molecules.

Thus, after the array is made, it is "decoded" in order to identify the location of the target sets, i.e. each subpopulation of beads, on the substrate surface.

In a preferred embodiment, pyrosequencing techniques are used to decode the array, as is generally described in U.S. Ser. Nos. 60/160,927, 09/513,362 (U.S. Ser. No. 20030108867) 09/553,993 and 09/556,463, hereby expressly incorporated by reference.

In a preferred embodiment, a selective decoding system is used. In this case, only those microspheres exhibiting a change in the optical signal as a result of the binding of a readout probe are decoded. This is commonly done when the number of "hits", i.e. the number of sites to decode, is generally low. That is, the array is first scanned under experimental conditions in the absence of the readout probes. The solution containing the readout probes is added, and only those locations exhibiting a change in the optical signal are decoded. For example, the beads at either the positive or negative signal locations may be either selectively tagged or released from the array (for example through the use of photocleavable linkers), and subsequently sorted or enriched in a fluorescence-activated cell sorter (FACS). That is, either all the negative beads are released, and then the positive beads are either released or analyzed in situ, or alternatively all the positives are released and analyzed. Alternatively, the labels may comprise halogenated aromatic compounds, and detection of the label is done using for example gas chromatography, chemical tags, isotopic tags mass spectral tags.

As will be appreciated by those in the art, this may also be done in systems where the array is not decoded; i.e. there need not ever be a correlation of bead composition with location. In this embodiment, the beads are loaded on the array, and the assay is run. The "positives", i.e. those beads displaying a change in the optical signal as is more fully outlined below, are then "marked" to distinguish or separate them from the "negative" beads. This can be done in several ways, preferably using fiber optic arrays. In a preferred embodiment, each bead contains a fluorescent dye. After the assay and the identification of the "positives" or "active beads", light is shown down either only the positive fibers or only the negative fibers, generally in the presence of a light-activated reagent (typically dissolved oxygen). In the former case, all the active beads are photobleached. Thus, upon non-selective release of all the beads with subsequent sorting, for example using a fluorescence activated cell sorter (FACS) machine, the non-fluorescent active beads can be sorted from the fluorescent negative beads. Alternatively, when light is shown down the negative fibers, all the negatives are non-fluorescent and the positives are fluorescent, and sorting can proceed. The characterization of the attached capture probe may be done directly, for example using mass spectroscopy.

Alternatively, the identification may occur through the use of identifier moieties ("IMs"), which are similar to IBLs but need not necessarily bind to DBLs. That is, the composition of the IMs may serve as the identifier. Thus, for example, a specific combination of IMs can serve to code the bead, and be used to identify the agent on the bead upon release from the bead followed by subsequent analysis, for example using a gas chromatograph or mass spectroscope.

Alternatively, rather than having each bead contain a fluorescent dye, each bead comprises a nonfluorescent precursor to a fluorescent dye. For example, using photocleavable protecting groups, such as certain ortho-nitrobenzyl groups, on a fluorescent molecule, photoactivation of the fluorochrome can be done. After the assay, light is shown down again either the "positive" or the "negative" fibers, to distinguish these populations. The illuminated precursors are then chemically converted to a fluorescent dye. All the beads are then released from the array, with sorting, to form populations of fluorescent and non-fluorescent beads (either the positives and the negatives or vice versa).

In an alternate preferred embodiment, the sites of attachment of the beads (for example the wells) include a photopolymerizable reagent, or the photopolymerizable agent is added to the assembled array. After the test assay is run, light is shown down again either the "positive" or the "negative" fibers, to distinguish these populations. As a result of the irradiation, either all the positives or all the negatives are polymerized and trapped or bound to the sites, while the other population of beads can be released from the array.

In a preferred embodiment, the location of every target set is determined using decoder binding ligands (DBLs). As outlined above, DBLs are binding ligands that will bind to identifier binding ligands, preferably when the IBL is a nucleic acid or protein.

In a preferred embodiment, the capture probes are single-stranded nucleic acids and the DBL is a substantially complementary single-stranded nucleic acid that binds (hybridizes) to the decoder probe. A decoder probe that is substantially complementary to each identifier probe is made and used to decode the array. In this embodiment, the identifier probes and the decoder probes should be of sufficient length (and the decoding step run under suitable conditions) to allow specificity; i.e. each identifier probe binds to its corresponding decoder probe with sufficient specificity to allow the distinction of each identifier probe.

In a preferred embodiment, the DBLs are either directly or indirectly labeled, as is outlined herein for primary and secondary labels. In a preferred embodiment, the DBL is directly labeled, that is, the DBL comprises a label. In an alternate embodiment, the DBL is indirectly labeled; that is, a labeling binding ligand (LBL) that will bind to the DBL is used. In this embodiment, the labeling binding ligand-DBL pair can be as described above for IBL-DBL pairs.

Accordingly, the identification of the location of the individual beads (or subpopulations of beads) is done using one or more decoding steps comprising a binding between the labeled DBL and the IBL.

After decoding, the DBLs can be removed and the array can be used; however, in some circumstances, the removal of the DBL is not required (although it may be desirable in some circumstances). It should be noted that when the DBL/IBL pair comprises nucleic acids, the DBLs may be "melted" off. In the case of proteinaceous DBL/IBL pairs, for example when antibody/antigen pairs are used, it may be beneficial to have the IBLs attached using cleavable linkers. In addition, as outlined herein, decoding may be done either before the array is used to in an assay, during the assay, or after the assay.

In one embodiment, a single decoding step is done. In this embodiment, each DBL is labeled with a unique label, such that the the number of unique tags is equal to or greater than the number of target sets (although in some cases, "reuse" of the unique labels can be done, as described herein; similarly, minor variants of candidate probes can share the same decoder, if the variants are encoded in another dimension, i.e. in the bead size or label). For each bead or IBL, a DBL is made that will specifically bind to it and contains a unique tag, for example one or more fluorochromes. Thus, the identity of each DBL, both its composition (i.e. its sequence when it is a nucleic acid) and its label, is known. Then, by adding the DBLs to the array containing the target sets under conditions which allow the formation of complexes (termed hybridization complexes when the components are nucleic acids) between the DBLs and either the capture probes or the IBLs, the location of each DBL can be elucidated. This allows the identification of the location of each target set; the random array has been decoded. The DBLs can then be removed, if necessary, and the target sample applied.

In a preferred embodiment, the number of unique labels is less than the number of unique target sets, and thus a sequential series of decoding steps are used. In this embodiment, decoder probes are divided into n sets for decoding. The number of sets corresponds to the number of unique tags. Each decoder probe is labeled in n separate reactions with n distinct tags. All the decoder probes share the same n tags. The decoder probes are pooled so that each pool contains only one of the n tag versions of each decoder, and no two decoder probes have the same sequence of tags across all the pools. The number of pools required for this to be true is determined by the number of decoder probes and the n. Hybridization of each pool to the array generates a signal at every address. The sequential hybridization of each pool in turn will generate a unique, sequence-specific code for each candidate probe. This identifies the candidate probe at each address in the array. For example, if four tags are used, then 4×n sequential hybridizations can ideally distinguish $4^n$ sequences, although in some cases more steps may be required. After the hybridization of each pool, the hybrids are denatured and the decoder probes removed, so that the probes are rendered single-stranded for the next hybridization (although it is also possible to hybridize limiting amounts of target so that the available probe is not saturated. Sequential hybridizations can be carried out and analyzed by subtracting pre-existing signal from the previous hybridization).

An example is illustrative. Assuming an array of 16 probe nucleic acids (numbers 1–16), and four unique tags (four different fluors, for example; labels A–D). Decoder probes 1–16 are made that correspond to the probes on the beads. The first step is to label decoder probes 1–4 with tag A, decoder probes 5–8 with tag B, decoder probes 9–12 with tag C, and decoder probes 13–16 with tag D. The probes are mixed and the pool is contacted with the array containing the beads with the attached identifier probes. The location of each tag (and thus each decoder and identifier probe pair) is then determined. The first set of decoder probes are then removed. A second set is added, but this time, decoder probes 1, 5, 9 and 13 are labeled with tag A, decoder probes 2, 6, 10 and 14 are labeled with tag B, decoder probes 3, 7, 11 and 15 are labeled with tag C, and decoder probes 4, 8, 12 and 16 are labeled with tag D. Thus, those beads that contained tag A in both decoding steps contain identifier probe 1; tag A in the first decoding step and tag B in the second decoding step contain identifier probe 2; tag A in the first decoding step and tag C in the second step contain identifier probe 3; etc. In one embodiment, the decoder probes are labeled in situ; that is, they need not be labeled prior to the decoding reaction. In this embodiment, the incoming decoder probe is shorter than the identifier probe, creating a 5' "overhang" on the decoding probe. The addition of labeled ddNTPs (each labeled with a unique tag) and a polymerase will allow the addition of the tags in a sequence specific manner, thus creating a sequence-specific pattern of signals. Similarly, other modifications can be done, including ligation, etc.

In addition, since the size of the array will be set by the number of unique decoding binding ligands, it is possible to "reuse" a set of unique DBLs to allow for a greater number of test sites. This may be done in several ways; for example, by using some subpopulations that comprise optical signatures. Similarly, the use of a positional coding scheme within an array; different sub-bundles may reuse the set of DBLs. Similarly, one embodiment utilizes bead size as a coding modality, thus allowing the reuse of the set of unique DBLs for each bead size. Alternatively, sequential partial loading of arrays with beads can also allow the reuse of DBLs. Furthermore, "code sharing" can occur as well.

In a preferred embodiment, the DBLs may be reused by having some subpopulations of beads comprise optical signatures. In a preferred embodiment, the optical signature is generally a mixture of reporter dyes, preferably fluorescent. By varying both the composition of the mixture (i.e. the ratio of one dye to another) and the concentration of the dye (leading to differences in signal intensity), matrices of unique optical signatures may be generated. This may be done by covalently attaching the dyes to the surface of the beads, or alternatively, by entrapping the dye within the bead.

In a preferred embodiment, the encoding can be accomplished in a ratio of at least two dyes, although more encoding dimensions may be added in the size of the beads, for example. In addition, the labels are distinguishable from one another; thus two different labels may comprise different molecules (i.e. two different fluors) or, alternatively, one label at two different concentrations or intensity.

In a preferred embodiment, the dyes are covalently attached to the surface of the beads. This may be done as is generally outlined for the attachment of the target analytes, using functional groups on the surface of the beads. As will be appreciated by those in the art, these attachments are done to minimize the effect on the dye.

In a preferred embodiment, the dyes are non-covalently associated with the beads, generally by entrapping the dyes in the pores of the beads.

Additionally, encoding in the ratios of the two or more dyes, rather than single dye concentrations, is preferred since it provides insensitivity to the intensity of light used to interrogate the reporter dye's signature and detector sensitivity.

In a preferred embodiment, a spatial or positional coding system is done. In this embodiment, there are sub-bundles or subarrays (i.e. portions of the total array) that are utilized. By analogy with the telephone system, each subarray is an "area code", that can have the same tags (i.e. telephone numbers) of other subarrays, that are separated by virtue of the location of the subarray. Thus, for example, the same unique tags can be reused from bundle to bundle. Thus, the use of 50 unique tags in combination with 100 different subarrays can form an array of 5000 different target sets. In this embodiment, it becomes important to be able to identify one bundle from another; in general, this is done either manually or through the use of marker beads, i.e. beads containing unique tags for each subarray.

In alternative embodiments, additional encoding parameters can be added, such as microsphere size. For example, the use of different size beads may also allow the reuse of sets of DBLs; that is, it is possible to use microspheres of different sizes to expand the encoding dimensions of the microspheres. Optical fiber arrays can be fabricated containing pixels with different fiber diameters or cross-sections; alternatively, two or more fiber optic bundles, each with different cross-sections of the individual fibers, can be added together to form a larger bundle; or, fiber optic bundles with fiber of the same size cross-sections can be used, but just with different sized beads. With different diameters, the largest wells can be filled with the largest microspheres and then moving onto progressively smaller microspheres in the smaller wells until all size wells are then filled. In this manner, the same dye ratio could be used to encode microspheres of different sizes thereby expanding the number of different oligonucleotide sequences or chemical functionalities present in the array. Although outlined for fiber optic substrates, this as well as the other methods outlined herein can be used with other substrates and with other attachment modalities as well.

In a preferred embodiment, the coding and decoding is accomplished by sequential loading of the microspheres into the array. As outlined above for spatial coding, in this embodiment, the optical signatures can be "reused". In this embodiment, the library of microspheres each comprising a different target set (or the subpopulations each comprise a different target set) is divided into a plurality of sublibraries; for example, depending on the size of the desired array and the number of unique tags, 10 sublibraries each comprising roughly 10% of the total library may be made, with each sublibrary comprising roughly the same unique tags. Then, the first sublibrary is added to the fiber optic bundle comprising the wells, and the location of each target set is determined, generally through the use of DBLs. The second sublibrary is then added, and the location of each target set is again determined. The signal in this case will comprise the signal from the "first" DBL and the "second" DBL; by comparing the two matrices the location of each bead in each sublibrary can be determined. Similarly, adding the third, fourth, etc. sublibraries sequentially will allow the array to be filled.

In a preferred embodiment, decoding of self-assembled random arrays is done on the bases of pH titration. In this embodiment, in addition to target analytes, the beads comprise optical signatures, wherein the optical signatures are generated by the use of pH-responsive dyes (sometimes referred to herein as "ph dyes") such as fluorophores. This embodiment is similar to that outlined in WO98/40726 and U.S. Pat. No. 6,327,410, both of which are expressly incorporated by reference, except that the dyes used in the present invention exhibits changes in fluorescence intensity (or other properties) when the solution pH is adjusted from below the pKa to above the pKa (or vice versa). In a preferred embodiment, a set of pH dyes are used, each with a different pKa, preferably separated by at least 0.5 pH units. Preferred embodiments utilize a pH dye set of pka's of 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11, and 11.5. Each bead can contain any subset of the pH dyes, and in this way a unique code for the target set is generated. Thus, the decoding of an array is achieved by titrating the array from pH 1 to pH 13, and measuring the fluorescence signal from each bead as a function of solution pH.

In some embodiments, as is outlined herein, the target sequence may not be the sample target sequence but instead is a product of a reaction herein, sometimes referred to herein as a "secondary" or "derivative" target sequence. Thus, for example, in LCR amplification reactions, the ligated probes can serve as a target sequence; similarly, in invasive cleavage variations, the cleaved detection sequence may serve as the target sequence.

Once made, the compositions of the invention find use in a variety of applications. As will be appreciated by those in the art, the systems of the invention may take on a large number of different configurations for a variety of purposes. In a preferred embodiment, the arrays are used to detect the presence or absence of sequences, such as genes, in a sample. Thus for example, the presence or absence of chromosomal aberations such as deletions or duplications can be monitored in tumor samples. In a preferred embodiment, genotyping reactions can be done. In addition, in any reaction, quantitation of the amount of a target sequence may be done. While the discussion below focuses on genotyping reactions, the discussion applies equally to detecting the presence of target sequences and/or their quantification.

In a preferred embodiment, the compositions find use in the detection and analysis of genotypes of one or more patients. In this embodiment, a variety of single nucleotide polymorphisms (SNPs) can be analyzed using the present systems. Thus, as is more fully outlined below, the target sequence comprises a position for which sequence information is desired, generally referred to herein as the "detection position" or "detection locus". In a preferred embodiment, the detection position is a single nucleotide, although in some embodiments, it may comprise a plurality of nucleotides, either contiguous with each other or separated by one or more nucleotides. By "plurality" as used herein is meant at least two. As used herein, the base which basepairs with a detection position base in a hybrid is termed a "readout position" or an "interrogation position".

These genotyping reactions are generally classified into 5 basic categories, as outlined below. In general, all of these reactions rely on the use of variety of different types of readout probes that hybridize to individual target sequences within a target set.

Simple Hybridization Genotyping

In a preferred embodiment, straight hybridization methods are used to elucidate the identity of the base at the detection position. Generally speaking, these techniques break down into two basic types of reactions: those that rely on competitive hybridization techniques, and those that discriminate using stringency parameters and combinations thereof.

Competitive Hybridization

In a preferred embodiment, the use of competitive hybridization probes (generally referred to herein as "readout probes") is done to elucidate either the identity of the nucleotide(s) at the detection position or the presence of a mismatch. For example, sequencing by hybridization has been described (Drmanac et al., Genomics 4:114 (1989); Koster et al., Nature Biotechnology 14:1123 (1996); U.S. Pat. Nos. 5,525,464; 5,202,231 and 5,695,940, among others, all of which are hereby expressly incorporated by reference in their entirety).

It should be noted in this context that "mismatch" is a relative term and meant to indicate a difference in the identity of a base at a particular position, termed the "detection position" herein, between two sequences. In general, sequences that differ from wild type sequences are referred to as mismatches. However, particularly in the case of SNPs, what constitutes "wild type" may be difficult to determine as multiple alleles can be relatively frequently observed in the population, and thus "mismatch" in this context requires the artificial adoption of one sequence as a standard. Thus, for the purposes of this invention, sequences are referred to herein as "match" and "mismatch". Thus, the present invention may be used to detect substitutions, insertions or deletions as compared to a wild-type sequence. In general, probes of the present invention are designed to be complementary to a target sequence, such that hybridization of the target and the probes of the present invention occurs. This complementarily need not be perfect; there may be any number of base pair mismatches that will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under the selected reaction conditions.

In a preferred embodiment, a plurality of probes (sometimes referred to herein as "readout probes" or "detection probes") are used to identify the base at the detection position. In this embodiment, each different readout probe comprises a different detection label (which, as outlined below, can be either a primary label or a secondary label) and a different base at the position that will hybridize to the detection position of the target sequence (herein referred to as the readout position) such that differential hybridization will occur. That is, all other parameters being equal, a perfectly complementary readout probe (a "match probe") will in general be more stable and have a slower off rate than a probe comprising a mismatch (a "mismatch probe") at any particular temperature.

Accordingly, by using different readout probes, each with a different base at the readout position and each with a different label, the identification of the base at the detection position is elucidated.

In one embodiment the readout probes are the same length. Preferably the probes have a similar melting temperature (Tm), although this is not required. In an alternative embodiment, readout probes as described herein need not be of the same length. That is, readout probes can be of different lengths. Using readout probes of different lengths provides the advantage that in varying the length of the probes, the Tm of the probes can be adjusted. This is beneficial in allowing uniform assay conditions can be used.

The readout probes comprise a detection label. By "detection label" or "detectable label" herein is meant a moiety that allows detection. This may be a primary label (which can be directly detected) or a secondary label (which is indirectly detected).

A primary label is one that can be directly detected, such as a fluorophore. In general, labels fall into three classes: a) isotopic labels, which may be radioactive or heavy isotopes; b) magnetic, electrical, thermal labels; and c) colored or luminescent dyes. Preferred labels include chromophores or phosphors but are preferably fluorescent dyes. Suitable dyes for use in the invention include, but are not limited to, fluorescent lanthanide complexes, including those of Europium and Terbium, fluorescein, rhodamine, tetramethylrhodamine, eosin, erythrosin, coumarin, methyl-coumarins, quantum dots (also referred to as "nanocrystals"), pyrene, Malacite green, stilbene, Lucifer Yellow, Cascade Blue™, Cy dyes (Cy3, Cy5, etc.), Texas Red, phycoerythrin, Bodipy, Alexa dyes and others described in the 6th Edition of the Molecular Probes Handbook by Richard P. Haugland, hereby expressly incorporated by reference. In a preferred embodiment, the detection label used for competitive hybridization is a primary label.

In a preferred embodiment, the detectable label is a secondary label. A secondary label is one that is indirectly detected; for example, a secondary label can bind or react with a primary label for detection, can act on an additional product to generate a primary label (e.g. enzymes), or may allow the separation of the compound comprising the secondary label from unlabeled materials, etc. Secondary labels find particular use in systems requiring separation of labeled and unlabeled probes, such as SBE, OLA, invasive cleavage, etc. reactions; in addition, these techniques may be used with many of the other techniques described herein. Secondary labels include, but are not limited to, one of a binding partner pair; chemically modifiable moieties; nuclease inhibitors, enzymes such horseradish peroxidase, alkaline phosphatases, luciferases, etc.

In a preferred embodiment, the secondary label is a binding partner pair. For example, the label may be a hapten or antigen, which will bind its binding partner. For example, suitable binding partner pairs include, but are not limited to: antigens (such as proteins (including peptides)) and antibodies (including fragments thereof (FAbs, etc.)); proteins and small molecules, including biotin/streptavidin and digoxygenin and antibodies; enzymes and substrates or inhibitors; other protein—protein interacting pairs; receptor-ligands; and carbohydrates and their binding partners, are also suitable binding pairs. Nucleic acid—nucleic acid binding proteins pairs are also useful. In general, the smaller of the pair is attached to the NTP (or the probe) for incorporation into the extension primer. Preferred binding partner pairs include, but are not limited to, biotin (or imino-biotin) and streptavidin, digeoxinin and Abs, and Prolinx™ reagents (see www.prolinxinc.com/ie4/home.hmtl).

In a preferred embodiment, the binding partner pair comprises a primary detection label (attached to the NTP and therefore to the extended primer) and an antibody that will specifically bind to the primary detection label. By "specifically bind" herein is meant that the partners bind with specificity sufficient to differentiate between the pair and other components or contaminants of the system. The binding should be sufficient to remain bound under the conditions of the assay, including wash steps to remove non-specific binding. In some embodiments, the dissociation constants of the pair will be less than about $10^{-4}$–$10^{-6}$ $M^{-1}$, with less than about $10^{-5}$ to $10^{-9}$ $M^{-1}$ being preferred and less than about $10^{-7}$–$10^{-9}$ $M^{-1}$ being particularly preferred.

In addition, the secondary label can be a chemically modifiable moiety. In this embodiment, labels comprising reactive functional groups are incorporated into the nucleic acid. Subsequently, primary labels, also comprising functional groups, may be added to these reactive groups. As is known in the art, this may be accomplished in a variety of ways. Preferred functional groups for attachment are amino groups, carboxy groups, oxo groups and thiol groups, with amino groups being particularly preferred. Using these functional groups, the primary labels can be attached using functional groups on the enzymes. For example, primary labels containing amino groups can be attached to secondary labels comprising amino groups, for example using linkers as are known in the art; for example, homoor heterobifunctional linkers as are well known (see 1994 Pierce Chemical Company catalog, technical section on cross-linkers, pages 155–200, incorporated herein by reference).

Accordingly, a detectable label is incorporated into the readout probe. In a preferred embodiment, a set of readout probes are used, each comprising a different base at the readout position. In some embodiments, each readout probe comprises a different label, that is distinguishable from the others. For example, a first label may be used for probes comprising adenosine at the readout position, a second label may be used for probes comprising guanine at the readout position, etc. In a preferred embodiment, the length and sequence of each readout probe is identical except for the readout position, although this need not be true in all embodiments.

The number of readout probes used will vary depending on the end use of the assay. For example, many SNPs are biallelic, and thus two readout probes, each comprising an interrogation base that will basepair with one of the detection position bases. For sequencing, for example, for the discovery of SNPs, a set of four readout probes are used.

Stringency Variation

In a preferred embodiment, sensitivity to variations in stringency parameters are used to determine either the identity of the nucleotide(s) at the detection position or the presence of a mismatch. As a preliminary matter, the use of different stringency conditions such as variations in temperature and buffer composition to determine the presence or absence of mismatches in double stranded hybrids comprising a single stranded target sequence and a probe is well known.

With particular regard to temperature, as is known in the art, differences in the number of hydrogen bonds as a function of basepairing between perfect matches and mismatches can be exploited as a result of their different Tms (the temperature at which 50% of the hybrid is denatured). Accordingly, a hybrid comprising perfect complementarity will melt at a higher temperature than one comprising at least one mismatch, all other parameters being equal. (It should be noted that for the purposes of the discussion herein, all other parameters (i.e. length of the hybrid, nature of the backbone (i.e. naturally occuring or nucleic acid analog), the assay solution composition and the composition of the bases, including G-C content are kept constant). However, as will be appreciated by those in the art, these factors may be varied as well, and then taken into account.)

In general, as outlined herein, high stringency conditions are those that result in perfect matches remaining in hybridization complexes, while imperfect matches melt off. Similarly, low stringency conditions are those that allow the formation of hybridization complexes with both perfect and imperfect matches. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. In another embodiment, less stringent hybridization conditions are used; for example, moderate or low stringency conditions may be used, as are known in the art; see Maniatis and Ausubel, supra, and Tijssen, supra.

As will be appreciated by those in the art, mismatch detection using temperature may proceed in a variety of ways, and is similar to the use of readout probes as outlined above. Again, as outlined above, a plurality of readout probes may be used in a sandwich format; in this embodiment, all the probes may bind at permissive, low temperatures (temperatures below the Tm of the mismatch); however, repeating the assay at a higher temperature (above the Tm of the mismatch) only the perfectly matched probe may bind. Thus, this system may be run with readout probes with different detectable labels, as outlined above. Alternatively, a single probe may be used to query whether a particular base is present.

Similarly, variations in buffer composition may be used to elucidate the presence or absence of a mismatch at the detection position. Suitable conditions include, but are not limited to, formamide concentration. Thus, for example, "low" or "permissive" stringency conditions include formamide concentrations of 0 to 10%, while "high" or "stringent" conditions utilize formamide concentrations of $\geq 40\%$. Low stringency conditions include NaCl concentrations of $\geq 1$ M, and high stringency conditions include concentrations of $\leq 0.3$ M. Furthermore, low stringency conditions include $MgCl_2$ concentrations of $\geq 10$ mM, moderate stringency as 1–10 mM, and high stringency conditions include concentrations of $\leq 1$ mM.

In this embodiment, as for temperature, a plurality of readout probes may be used, with different bases in the readout position (and optionally different labels). Running the assays under the permissive conditions and repeating under stringent conditions will allow the elucidation of the base at the detection position.

In one embodiment, the probes used as readout probes are "Molecular Beacon" probes as are generally described in Whitcombe et al., Nature Biotechnology 17:804 (1999), hereby incorporated by reference. As is known in the art, Molecular Beacon probes form "hairpin" type structures, with a fluorescent label on one end and a quencher on the other. In the absence of the target sequence, the ends of the hairpin hybridize, causing quenching of the label. In the presence of a target sequence, the hairpin structure is lost in favor of target sequence binding, resulting in a loss of quenching and thus an increase in signal.

Extension Genotyping

In this embodiment, any number of techniques are used to add a nucleotide to the readout position of an extension probe. By "extension probe" is meant a probe hybridized to the target sequence adjacent to the detection position. Extension probes also are included in the definition of readout probes. By relying on enzymatic specificity, preferentially a perfectly complementary base is added. All of these methods rely on the enzymatic incorporation of nucleotides at the detection position. This may be done using chain terminating dNTPs, such that only a single base is incorporated (e.g. single base extension methods), or under conditions that only a single type of nucleotide is added followed by identification of the added nucleotide (extension and pyrosequencing techniques).

Single Base Extension

In a preferred embodiment, single base extension (SBE; sometimes referred to as "minisequencing") is used to determine the identity of the base at the detection position. Briefly, SBE is a technique that utilizes an extension primer (also included withing the definition of readout probe) that hybridizes to the target nucleic acid immediately adjacent to the detection position. A polymerase (generally a DNA polymerase) is used to extend the 3' end of the primer with a nucleotide analog labeled a detection label as described herein. Based on the fidelity of the enzyme, a nucleotide is only incorporated into the readout position of the growing nucleic acid strand if it is perfectly complementary to the base in the target strand at the detection position. The nucleotide may be derivatized such that no further extensions can occur, so only a single nucleotide is added. Once the labeled nucleotide is added, detection of the label proceeds as outlined herein. See generally Sylvanen et al., Genomics 8:684692 (1990); U.S. Pat. Nos. 5,846,710 and 5,888,819; Pastinen et al., Genomics Res. 7(6):606–614 (1997); all of which are expressly incorporated herein by reference.

The reaction is initiated by introducing the assay complex comprising the target sequence (i.e. the array) to a solution comprising a first nucleotide. By "nucleotide" in this context herein is meant a deoxynucleoside-triphosphate (also called deoxynucleotides or dNTPs, e.g. dATP, dTTP, dCTP and dGTP). In general, the nucleotides comprise a detectable label, which may be either a primary or a secondary label. In addition, the nucleotides may be nucleotide analogs, depending on the configuration of the system. For example, if the dNTPs are added in sequential reactions, such that only a single type of dNTP can be added, the nucleotides need not be chain terminating. In addition, in this embodiment, the dNTPs may all comprise the same type of label.

Alternatively, if the reaction comprises more than one dNTP, the dNTPs should be chain terminating, that is, they have a blocking or protecting group at the 3' position such that no further dNTPs may be added by the enzyme. As will be appreciated by those in the art, any number of nucleotide analogs may be used, as long as a polymerase enzyme will still incorporate the nucleotide at the readout position. Preferred embodiments utilize dideoxy-triphosphate nucleotides (ddNTPs) and halogenated dNTPs. Generally, a set of nucleotides comprising ddATP, ddCTP, ddGTP and ddTTP is used, each with a different detectable label, although as outlined herein, this may not be required.

In a preferred embodiment, the nucleotide analogs comprise a detectable label, which can be either a primary or secondary detectable label. Preferred primary labels are those outlined above for interrogation labels. However, the enzymatic incorporation of nucleotides comprising fluorophores is may be poor under many conditions; accordingly, a preferred embodiment utilizes secondary detectable labels. In addition, as outlined below, the use of secondary labels may also facilitate the removal of unextended probes.

In addition, as will be appreciated by those in the art, the single base extension reactions of the present invention allow the precise incorporation of modified bases into a growing nucleic acid strand. Thus, any number of modified nucleotides may be incorporated for any number of reasons, including probing structure-function relationships (e.g. DNA:DNA or DNA:protein interactions), cleaving the nucleic acid, crosslinking the nucleic acid, incorporate mismatches, etc.

In addition to a first nucleotide, the solution also comprises an extension enzyme, generally a DNA polymerase. Suitable DNA polymerases include, but are not limited to, the Klenow fragment of DNA polymerase I, SEQUENASE 1.0 and SEQUENASE 2.0 (U.S. Biochemical), T5 DNA polymerase and Phi29 DNA polymerase. If the NTP is complementary to the base of the detection position of the target sequence, which is adjacent to the extension primer, the extension enzyme will add it to the extension primer at the readout position. Thus, the extension primer is modified, i.e. extended, to form a modified primer, sometimes referred to herein as a "newly synthesized strand". If desired, the temperature of the reaction can be adjusted (or cycled) such that amplification occurs, generating a plurality of modified primers.

In addition, since unextended primers do not comprise labels, the unextended primers need not be removed. However, they may be, if desired, as outlined below; for example, if a large excess of primers are used, there may not be sufficient signal from the extended primers competing for binding to the surface.

As will be appreciated by those in the art, the determination of the base at the detection position can proceed in several ways. In a preferred embodiment, the reaction is run with all four nucleotides (assuming all four nucleotides are required), each with a different label, as is generally outlined herein.

Alternatively, a single label is used, by using four reactions: this may be done either by using a single substrate and sequential reactions, or by using four arrays. For example, dATP can be added to the assay complex, and the generation of a signal evaluated; the dATP can be removed and dTTP added, etc. Alternatively, four arrays can be used; the first is reacted with dATP, the second with dTTP, etc., and the presence or absence of a signal evaluated.

Alternatively, ratiometric analysis can be done; for example, two labels, "A" and "B", on two substrates (e.g. two arrays) can be done. In this embodiment, two sets of primer extension reactions are performed, each on two arrays, with each reaction containing a complete set of four chain terminating NTPs. The first reaction contains two "A" labeled nucleotides and two "B" labeled nucleotides (for example, A and C may be "A" labeled, and G and T may be "B" labeled). The second reaction also contains the two labels, but switched; for example, A and G are "A" labeled and T and C are "B" labeled. This reaction composition allows a biallelic marker to be ratiometrically scored; that is, the intensity of the two labels in two different "color" channels on a single substrate is compared, using data from a set of two hybridized arrays. For instance, if the marker is A/G, then the first reaction on the first array is used to calculate a ratiometric genotyping score; if the marker is A/C, then the second reaction on the second array is used for the calculation; if the marker is G/T, then the second array is used, etc. This concept can be applied to all possible biallelic marker combinations. "Scoring" a genotype using a single fiber ratiometric score allows a much more robust genotyping than scoring a genotype using a comparison of absolute or normalized intensities between two different arrays.

Removal of Unextended Primers

In a preferred embodiment, for both SBE as well as a number of other reactions outlined herein, it is desirable to remove the unextended or unreacted primers from the assay mixture, and particularly from the array, as unextended primers will compete with the extended (labeled) primers in binding to capture probes, thereby diminishing the signal. The concentration of the unextended primers relative to the extended primer may be relatively high, since a large excess of primer is usually required to generate efficient primer annealing. Accordingly, a number of different techniques may be used to facilitate the removal of unextended primers. These generally include methods based on removal of unreacted primers by binding to a solid support, protecting the reacted primers and degrading the unextended ones, and separating the unreacted and reacted primers. While the discussion below applies specifically to SBE, these techniques may be used in any of the methods described herein.

Solid Phase Removal

In a preferred embodiment, the NTPs (or, in the case of other methods, one or more of the probes) comprise a secondary detectable label that can be used to separate extended and non-extended primers. As outlined above, detection labels may be primary labels (i.e. directly detectable) or secondary labels (indirectly detectable). Secondary labels find particular use in systems requiring separation of labeled and unlabeled probes, such as SBE, OLA, invasive cleavage, etc. reactions; in addition, these techniques may be used with many of the other techniques described herein.

In a preferred embodiment, the secondary label is a one of a binding partner pair. For example, a preferred embodiment utilizes binding partner pairs comprising biotin or imino-biotin and streptavidin, imino-biotin is particularly preferred when the methods require the later separation of the pair, as imino-biotin disassociates from streptavidin in pH 4.0 buffer while biotin requires harsh denaturants (e.g. 6 M guanidinium HCl, pH 1.5 or 90% formamide at 95° C.).

This may also be accomplished using chemically modifiable secondary labels. That is, in a preferred embodiment, the secondary label is a chemically modifiable moiety. In this embodiment, labels comprising reactive functional groups are incorporated into the nucleic acid. These functional groups are then used to remove the reacted primers, for example by attaching the reacted primers to a solid support, as outlined below, followed by a cleavage reaction and addition to the array.

In this embodiment, it is preferred that the other half of the binding pair is attached to a solid support. In this embodiment, the solid support may be any as described herein for substrates and microspheres, and the form is preferably microspheres as well; for example, a preferred embodiment utilizes magnetic beads that can be easily introduced to the sample and easily removed, although any affinity chromatography formats may be used as well. Standard methods are used to attach the binding partner to the solid support, and can include direct or indirect attachment methods. For example, biotin labeled antibodies to fluorophores can be attached to streptavidin coated magnetic beads.

Thus, in this embodiment, the extended primers comprise a binding member that is contacted with its binding partner under conditions wherein the extended primers are separated from the unextended primers. These extended primers can then be added to the array comprising target sets as described herein.

Protection and Degradation

In this embodiment, the dNTPs that are added during the reaction confer protection from degradation (whether chemical or enzymatic). Thus, after the assay, the degradation components are added, and unreacted primers are degraded, leaving only the reacted primers. Labeled protecting groups are particularly preferred; for example, 3'-substituted-2'-dNTPs can contain anthranylic derivatives that are fluorescent (with alkali or enzymatic treatment for removal of the protecting group).

In a preferred embodiment, the secondary label is a nuclease inhibitor, such as thiol NTPs. In this embodiment, the chain-terminating NTPs are chosen to render extended primers resistant to nucleases, such as 3'-exonucleases. Addition of an exonuclease will digest the non-extended primers leaving only the extended primers to bind to the target sequences on the array. This may also be done with OLA, wherein the ligated probe will be protected but the unprotected ligation probe will be digested.

In this embodiment, suitable 3'-exonucleases include, but are not limited to, exo I, exo III, exo VII, and 3'–5'exophosphodiesterases.

Alternatively, an 3' exonuclease may be added to a mixture of 3' labeled biotin/streptavidin; only the unreacted oligonucleotides will be degraded. Following exonuclease treatment, the exonuclease and the streptavidin can be degraded using a protease such as proteinase K. The surviving nucleic acids (i.e. those that were biotinylated) are then hybridized to the array.

Separation Systems

The use of secondary label systems (and even some primary label systems) can be used to separate unreacted and reacted probes; for example, the addition of streptavidin to a nucleic acid greatly increases its size, as well as changes its physical properties, to allow more efficient separation techniques. For example, the mixtures can be size fractionated by exclusion chromatography, affinity chromatography, filtration or differential precipitation.

Non-terminated Extension

In a preferred embodiment, methods of adding a single base are used that do not rely on chain termination. That is, similar to SBE, enzymatic reactions that utilize dNTPs and polymerases can be used; however, rather than use chain terminating dNTPs, regular dNTPs are used. This method relies on a time-resolved basis of detection; only one type of base is added during the reaction. Thus, for example, four different reactions each containing one of the dNTPs can be done; this is generally accomplished by using four different substrates, although as will be appreciated by those in the art, not all four reactions need occur to identify the nucleotide at a detection position. In this embodiment, the signals from single additions can be compared to those from multiple additions; that is, the addition of a single ATP can be distinguished on the basis of signal intensity from the addition of two or three ATPs. These reactions are accomplished as outlined above for SBE, using extension primers and polymerases; again, one label or four different labels can be used, although as outlined herein, the different NTPs must be added sequentially.

A preferred method of extension in this embodiment is pyrosequencing.

Pyrosequencing

Pyrosequencing is an extension method that can be used to add one or more nucleotides to the detection position(s); it is very similar to SBE except that chain terminating NTPs need not be used (although they may be). Pyrosequencing relies on the detection of a reaction product, PPi, produced during the addition of an NTP to a growing oligonucleotide chain, rather than on a label attached to the nucleotide. One molecule of PPi is produced per dNTP added to the extension primer. That is, by running sequential reactions with each of the nucleotides, and monitoring the reaction products, the identity of the added base is determined.

The release of pyrophosphate (PPi) during the DNA polymerase reaction can be quantitatively measured by many different methods and a number of enzymatic methods have been described; see Reeves et al., Anal. Biochem. 28:282 (1969); Guillory et al., Anal. Biochem. 39:170 (1971); Johnson et al., Anal. Biochem. 15:273 (1968); Cook et al., Anal. Biochem. 91:557 (1978); Drake et al., Anal. Biochem. 94:117 (1979); WO93/23564; WO 98/28440; WO98/13523; Nyren et al., Anal. Biochem. 151:504 (1985); all of which are incorporated by reference. The latter method allows continuous monitoring of PPi and has been termed ELIDA (Enzymatic Luminometric Inorganic Pyrophosphate Detection Assay). A preferred embodiment utilizes any method which can result in the generation of an optical signal, with preferred embodiments utilizing the generation of a chemiluminescent or fluorescent signal.

A preferred method monitors the creation of PPi by the conversion of PPi to ATP by the enzyme sulfurylase, and the subsequent production of visible light by firefly luciferase (see Ronaghi et al., Science 281:363 (1998), incorporated by reference). In this method, the four deoxynucleotides (dATP, dGTP, dCTP and dTTP; collectively dNTPs) are added stepwise to a partial duplex comprising a sequencing primer hybridized to a single stranded DNA template and incubated with DNA polymerase, ATP sulfurylase, luciferase, and optionally a nucleotide-degrading enzyme such as apyrase. A dNTP is only incorporated into the growing DNA strand if it is complementary to the base in the template strand. The synthesis of DNA is accompanied by the release of PPi equal in molarity to the incorporated dNTP. The PPi is converted to ATP and the light generated by the luciferase is directly proportional to the amount of ATP. In some cases the unincorporated dNTPs and the produced ATP are degraded between each cycle by the nucleotide degrading enzyme.

Accordingly, a preferred embodiment of the methods of the invention is as follows. A substrate comprising microspheres containing the target sequences and extension primers, forming hybridization complexes, is dipped or contacted with a reaction chamber or well comprising a single type of dNTP, an extension enzyme, and the reagents and enzymes necessary to detect PPi. If the dNTP is complementary to the base of the target portion of the target sequence adjacent to the extension primer, the dNTP is added, releasing PPi and generating detectable light, which is detected as generally described in U.S. Ser. Nos. 09/189, 543, U.S. Pat. No. 6,327,410, and PCT US98/09163, all of which are hereby incorporated by reference. If the dNTP is not complementary, no detectable signal results. The substrate is then contacted with a second reaction chamber comprising a different dNTP and the additional components of the assay. This process is repeated if the identity of a base at a second detection position is desirable.

In a preferred embodiment, washing steps, i.e. the use of washing chambers, may be done in between the dNTP reaction chambers, as required. These washing chambers may optionally comprise a nucleotide-degrading enzyme, to remove any unreacted dNTP and decreasing the background signal, as is described in WO 98/28440, incorporated herein by reference.

As will be appreciated by those in the art, the system can be configured in a variety of ways, including both a linear progression or a circular one; for example, four arrays may be used that each can dip into one of four reaction chambers arrayed in a circular pattern. Each cycle of sequencing and reading is followed by a 90 degree rotation, so that each substrate then dips into the next reaction well.

In a preferred embodiment, one or more internal control sequences are used. That is, at least one microsphere in the array comprises a known sequence that can be used to verify that the reactions are proceeding correctly. In a preferred embodiment, at least four control sequences are used, each of which has a different nucleotide at each position: the first control sequence will have an adenosine at position 1, the second will have a cytosine, the third a guanosine, and the fourth a thymidine, thus ensuring that at least one control sequence is "lighting up" at each step to serve as an internal control.

One additional benefit of pyrosequencing for genotyping purposes is that since the reaction does not rely on the incorporation of labels into a growing chain, the unreacted extension primers need not be removed.

Allelic PCR

In a preferred embodiment, the method used to detect the base at the detection position is allelic PCR, referred to herein as "aPCR". As described in Newton et al., Nucl. Acid Res. 17:2503 (1989), hereby expressly incoporated by reference, allelic PCR allows single base discrimination based on the fact that the PCR reaction does not proceed well if the terminal 3'-nucleotide is mismatched, assuming the DNA polymerase being used lacks a 3'-exonuclease proofreading activity. Accordingly, the identification of the base proceeds by using allelic PCR primers (sometimes referred to herein as aPCR primers) that have readout positions at their 3' ends. aPCR primers also are included within the definition of readout probes. Thus the target sequence comprises a first domain comprising at its 5' end a detection position.

In general, aPCR may be briefly described as follows. A double stranded target nucleic acid is denatured, generally by raising the temperature, and then cooled in the presence of an excess of a aPCR primer, which then hybridizes to the first target strand. If the readout position of the aPCR primer basepairs correctly with the detection position of the target sequence, a DNA polymerase (again, that lacks 3'-exonuclease activity) then acts to extend the primer with dNTPs, resulting in the synthesis of a new strand forming a hybridization complex. The sample is then heated again, to disassociate the hybridization complex, and the process is repeated. By using a second PCR primer for the complementary target strand, rapid and exponential amplification occurs. Thus aPCR steps are denaturation, annealing and extension. The particulars of aPCR are well known, and include the use of a thermostable polymerase such as Taq I polymerase and thermal cycling.

Accordingly, the aPCR reaction requires at least one aPCR primer, a polymerase, and a set of dNTPs. As outlined herein, the primers may comprise the label, or one or more of the dNTPs may comprise a label.

Furthermore, the aPCR reaction may be run as a competition assay of sorts. For example, for biallelic SNPs, a first aPCR primer comprising a first base at the readout position and a first label, and a second aPCR primer comprising a different base at the readout position and a second label, may be used. The PCR primer for the other strand is the same. The examination of the ratio of the two colors can serve to identify the base at the detection position.

Ligation Techniques for Genotyping

In this embodiment, the readout of the base at the detection position proceeds using a ligase. In this embodiment, it is the specificity of the ligase which is the basis of the genotyping; that is, ligases generally require that the 5' and 3' ends of the ligation probes have perfect complementarity to the target for ligation to occur. Ligation probes also are included within the definition of readout probes.

In a preferred embodiment, the identity of the base at the detection position proceeds utilizing the OLA. The method can be run at least two different ways; in a first embodiment, only one strand of a target sequence is used as a template for ligation; alternatively, both strands may be used; the latter is generally referred to as Ligation Chain Reaction or LCR. See generally U.S. Pat. Nos. 5,185,243 and 5,573,907; EP 0 320 308 B1; EP 0 336 731 B1; EP 0 439 182 B1; WO 90/01069; WO 89/12696; and WO 89/09835, and U.S. Ser. Nos. 60/078,102 and 60/073,011, all of which are incorporated by reference.

This method is based on the fact that two probes can be preferentially ligated together, if they are hybridized to a target strand and if perfect complementarity exists at the two bases being ligated together. Thus, in this embodiment, the target sequence comprises a contiguous first target domain comprising the detection position and a second target domain adjacent to the detection position. That is, the detection position is "between" the rest of the first target domain and the second target domain. A first ligation probe is hybridized to the first target domain and a second ligation probe is hybridized to the second target domain. If the first ligation probe has a base perfectly complementary to the detection position base, and the adjacent base on the second probe has perfect complementarity to its position, a ligation structure is formed such that the two probes can be ligated together to form a ligated probe. If this complementarity does not exist, no ligation structure is formed and the probes are not ligated together to an appreciable degree. In addition, as is more fully outlined below, this method may also be done using ligation probes that are separated by one or more nucleotides, if dNTPs and a polymerase are added (this is sometimes referred to as "Genetic Bit" analysis).

In a preferred embodiment, LCR is done for two strands of a double-stranded target sequence. The target sequence is denatured, and two sets of probes are added: one set as outlined above for one strand of the target, and a separate set (i.e. third and fourth primer probe nucleic acids) for the other strand of the target, both of which are part of a particular target set.

As will be appreciated by those in the art, the ligation product can be detected in a variety of ways. Preferably, detection is accomplished by removing the unligated labeled probe from the reaction. In one embodiment, the unligated probes are removed by digesting 3' non-protected oligonucleotides with a 3' exonuclease, such as, exonuclease 1. The ligation products are protected from exo I digestion by including, for example, the use of a number of sequential phosphorothioate residues at their 3' terminus (for example at least four), thereby, rendering them resistant to exonuclease digestion. The unligated detection oligonucleotides are not protected and are digested.

Alternatively, the OLA assay is performed and unligated oligonucleotides are removed by washing under appropriate stringency to remove unligated oligonucleotides. By having one of the probes comprise a label, detection is achieved.

Again, as outlined above for SBE, unreacted ligation primers may be removed from the mixture as needed. For example, the first ligation probe may comprise the label (either a primary or secondary label) and the second may be blocked at its 3' end with an exonuclease blocking moiety; after ligation and the introduction of the nuclease, the labeled ligation probe will be digested, leaving the ligation product and the second probe; however, since the second probe is unlabeled, it is effectively silent in the assay. Similarly, the second probe may comprise a binding partner used to pull out the ligated probes, leaving unligated labeled ligation probes behind. The binding pair is then disassociated and added to the array.

Padlock Probe Ligation

In a preferred embodiment, the ligation probes are specialized probes called "padlock probes" (which also are within the definition of readout probes) Nilsson et al, 1994, Science 265:2085. These probes have a first ligation domain that is identical to a first ligation probe, in that it hybridizes to a first target sequence domain, and a second ligation domain, identical to the second ligation probe, that hybridizes to an adjacent target sequence domain. Again, as for OLA, the detection position can be either at the 3' end of the first ligation domain or at the 5' end of the second ligation domain. However, the two ligation domains are connected by a linker, frequently nucleic acid. The configuration of the system is such that upon ligation of the first and second ligation domains of the padlock probe, the probe forms a circular probe, and forms a complex with the target sequence wherein the target sequence is "inserted" into the loop of the circle.

In this embodiment, the unligated probes may be removed through degradation (for example, through a nuclease), as there are no "free ends" in the ligated probe.

Cleavage Techniques for Genotyping

In a preferred embodiment, the specificity for genotyping is provided by a cleavage enzyme. There are a variety of enzymes known to cleave at specific sites, either based on sequence specificity, such as restriction endonucleases, or using structural specificity, such as is done through the use of invasive cleavage technology.

Endonuclease Techniques

In a preferred embodiment, enzymes that rely on sequence specificity are used. In general, these systems rely on the cleavage of double stranded sequence containing a specific sequence recognized by a nuclease, preferably an endonuclease.

These systems may work in a variety of ways. In one embodiment, a labeled readout probe is used; the binding of the target sequence forms a double stranded sequence that a restriction endonuclease can then recognize and cleave, if the correct sequence is present. The cleavage results in the loss of the label, and thus a loss of signal.

Alternatively, as will be appreciated by those in the art, a labeled target sequence may be used as well; for example, a labeled primer may be used in the PCR amplification of the target, such that the label is incorporated in such a manner as to be cleaved off by the enzyme.

Alternatively, the readout probe (or, again, the target sequence) may comprise both a fluorescent label and a quencher, as is known in the art. In this embodiment, the label and the quencher are attached to different nucleosides, yet are close enough that the quencher molecule results in little or no signal being present. Upon the introduction of the enzyme, the quencher is cleaved off, leaving the label, and allowing signaling by the label.

Furthermore, there are some systems that do not require cleavage for detection; for example, some nucleic acid binding proteins will bind to specific sequences and can thus serve as a secondary label. For example, some transcription factors will bind in a highly sequence dependent manner, and can distinguish between two SNPs. Having bound to the hybridization complex, a detectable binding partner can be added for detection.

In addition, as will be appreciated by those in the art, this type of approach works with other cleavage methods as well, for example the use of invasive cleavage methods, as outlined below.

Invasive Cleavage

In a preferred embodiment, the determination of the identity of the base at the detection position of the target sequence proceeds using invasive cleavage technology. In general, invasive cleavage techniques rely on the use of structure-specific nucleases, where the structure can be formed as a result of the presence or absence of a mismatch. Generally, invasive cleavage technology may be described as follows. A target nucleic acid is recognized by two distinct probes. At least one of these probes is within the definition of a readout probe. A first probe, generally referred to herein as an "invader" probe, is substantially complementary to a first portion of the target nucleic acid. A second probe, generally referred to herein as a "signal probe", is partially complementary to the target nucleic acid; the 3' end of the signal oligonucleotide is substantially complementary to the target sequence while the 5' end is non-complementary and preferably forms a single-stranded "tail" or "arm". Hybridization of the first and second oligonucleotides near or adjacent to one another on the target nucleic acid forms a number of structures. In a preferred embodiment, a forked cleavage structure, forms and is a substrate of a nuclease which cleaves off a portion of the signal oligonucleotide. The site of cleavage is controlled by the distance or overlap between the 3' end of the invader oligonucleotide and the downstream fork of the signal oligonucleotide. Therefore, neither oligonucleotide is subject to cleavage when misaligned or when unattached to target nucleic acid.

In a preferred embodiment, the signalling probe comprises both a fluorophore label (attached to the portion of the signalling probe that hybridizes to the target) and a quencher (generally on the detection sequence), with a cleavage site in between. Thus, in the absence of cleavage, very little signal is seen due to the quenching reaction. After cleavage, however, the detection sequence is removed, along with the quencher, leaving the unquenched fluorophore. In a preferred embodiment, it is the 3' end of the signalling probe that is attached to the bead (although as will be appreciated by those in the art, the system can be configured in a variety of different ways, including methods that would result in a loss of signal upon cleavage). Thus, the quencher molecule is located 5' to the cleavage site. Upon assembly of an assay complex, comprising the target sequence, an invader probe, and a signalling probe, and the introduction of the cleavage enzyme, the cleavage of the complex results in the dissociation of the quencher from the complex, resulting in an increase in fluorescence.

In this embodiment, suitable fluorophore-quencher pairs are as known in the art. For example, suitable quencher molecules comprise Dabcyl.

In a preferred embodiment, the nuclease that recognizes the forked cleavage structure and catalyzes release of the tail is thermostable, thereby, allowing thermal cycling of the cleavage reaction, if desired, although iosthermal reactions are preferred. Preferred nucleases derived from thermostable DNA polymerases that have been modified to have reduced synthetic activity which is an unnecessary side-reaction during cleavage are disclosed in U.S. Pat. Nos. 5,719,028 and 5,843,669, hereby expressly by reference. The synthetic activity of the DNA polymerase is reduced to a level where it does not interfere with detection of the cleavage reaction and detection of the freed tail. Preferably the DNA polymerase has no detectable polymerase activity. Examples of nucleases are those derived from *Thermus aquaticus, Thermus flavus*, or *Thermus thermophilus*.

In another embodiment, thermostable structure-specific nucleases are Flap endonucleases (FENs) selected from FEN-1 or FEN-2 like (e.g. XPG and RAD2 nucleases) from Archaebacterial species, for example, FEN-1 from *Methanococcus jannaschii, Pyrococcus furiosis, Pyrococcus woesei*, and *Archaeoglobus fulgidus*. (U.S. Pat. No. 5,843, 669 and Lyamichev et al. 1999. Nature Biotechnology 17:292–297; both of which are hereby expressly by reference).

In a preferred embodiment, the nuclease is AfuFEN1 or PfuFEN1 nuclease. To cleave a forked structure, these nucleases require at least one overlapping nucleotide between the signal and invasive probes to recognize and cleave the 5' end of the signal probe. To effect cleavage the 3'-terminal nucleotide of the invader oligonucleotide is not required to be complementary to the target nucleic acid. In contast, mismatch of the signal probe one base upstream of the cleavage site prevents creation of the overlap and cleavage. The specificity of the nuclease reaction allows single nucleotide polymorphism (SNP) detection from, for example, genomic DNA, as outlined below (Lyamichev et al.).

In addition, as for most of the techniques outlined herein, these techniques may be done for the two strands of a double-stranded target sequence. The target sequence is denatured, and two sets of probes are added: one set as outlined above for one strand of the target, and a separate set for the other strand of the target.

Thus, the invasive cleavage reaction requires, in no particular order, an invader probe, a signalling probe, and a cleavage enzyme.

Other suitable reactions are outlined in U.S. Ser. Nos. 09/425,633, 09/535,854, 09/553,993 and 09/556,463, hereby expressly incorporated by reference. In particular, combinations of these techniques may be used, as long as the assay remains a solid-phase assay. For example, combinations of any of the genotyping reactions with OLA or SBE maybe done; for example, an OLA reaction plus SBE can be done; an invasive cleavage reaction plus SBE can be done, etc. That is, in one embodiment, a combination techniques or assays can be performed. Performing multiple assays provides the advantage of increasing the confidence, accuracy and/or reliability of analysis. See the section on combination techniques in U.S. Ser. No. 09/425,633, hereby expressly incorporated by reference. Additional modifications of the assays outlined herein include analyzing both strands of a target sequence, when the target analyte is a nucleic acid. Again, analyzing both strands serves to increase accuracy and reliability of analysis.

In addition the invention includes methods of increasing the efficiency of analyzing multiple patient samples. In one embodiment the method includes performing a first analysis on an array with a pool of probes. That is, analyzing a pool of target analytes with a pool of readout probes. Upon detecting a positive signal from one of the pooled probes, a subsequent analysis can be performed with individual probes. This method finds particular use in analyzing less common alleles.

In addition, a variety of fluid handling techniques find use in the present invention. For example, a variety of microfluidics techniques, such as are generally outlined in U.S. Ser. No. 09/316,154 (U.S. Pat. No. 200020051971), hereby expressly incorporated by reference. In particular, a system that utilizes a chamber comprising the discrete sites, i.e. wells. The beads are loaded into the chamber using a microfluidic system as generally described in U.S. Ser. Nos. 09/316,154 (U.S. Pat. No. 20020051971), 60/252,227and WO00/71243.

In addition, a variety of detectors find use in the present invention. In a preferred embodiment existing scanning-based instrumentation including, but not limited to, that sold by General Scanning, Molecular Dynamics, Gene Machine, Genetic Microsystems, Vysis, Axon and Hewlett-Packard can be used to analyze arrays of the present invention. In addition, detectors coupled to fiber optic bundles are used as described in WO 00/16101.

In an alternative embodiment, detection is accomplished not while the beads are on a solid surface, but rather the beads are analyzed while in solution. That is, the beads can be decoded and/or analyzed by flow cytometry, for example.

All references cited herein are incorporated by reference.

EXAMPLES

Example 1

Experimental design for amplicon immobilization and hybridization to streptavidin beads.

NHS-activate amino-modified silica beads and attach streptavidin (25 µg/mg of beads).

Immobilize biotin-labeled amplicon to streptavidin beads by incubating for 20 minutes.

Denature amplicon on streptavidin bead with 0.1 M NaOH.

Wash beads in hybridization buffer –0.6× SSC+0.1% Tween 20.

Hybridize to amplicon complementary (fluorescein-labeled) oligo at 50 nanomolar at room temperature for 120 minutes.

Figure 2:
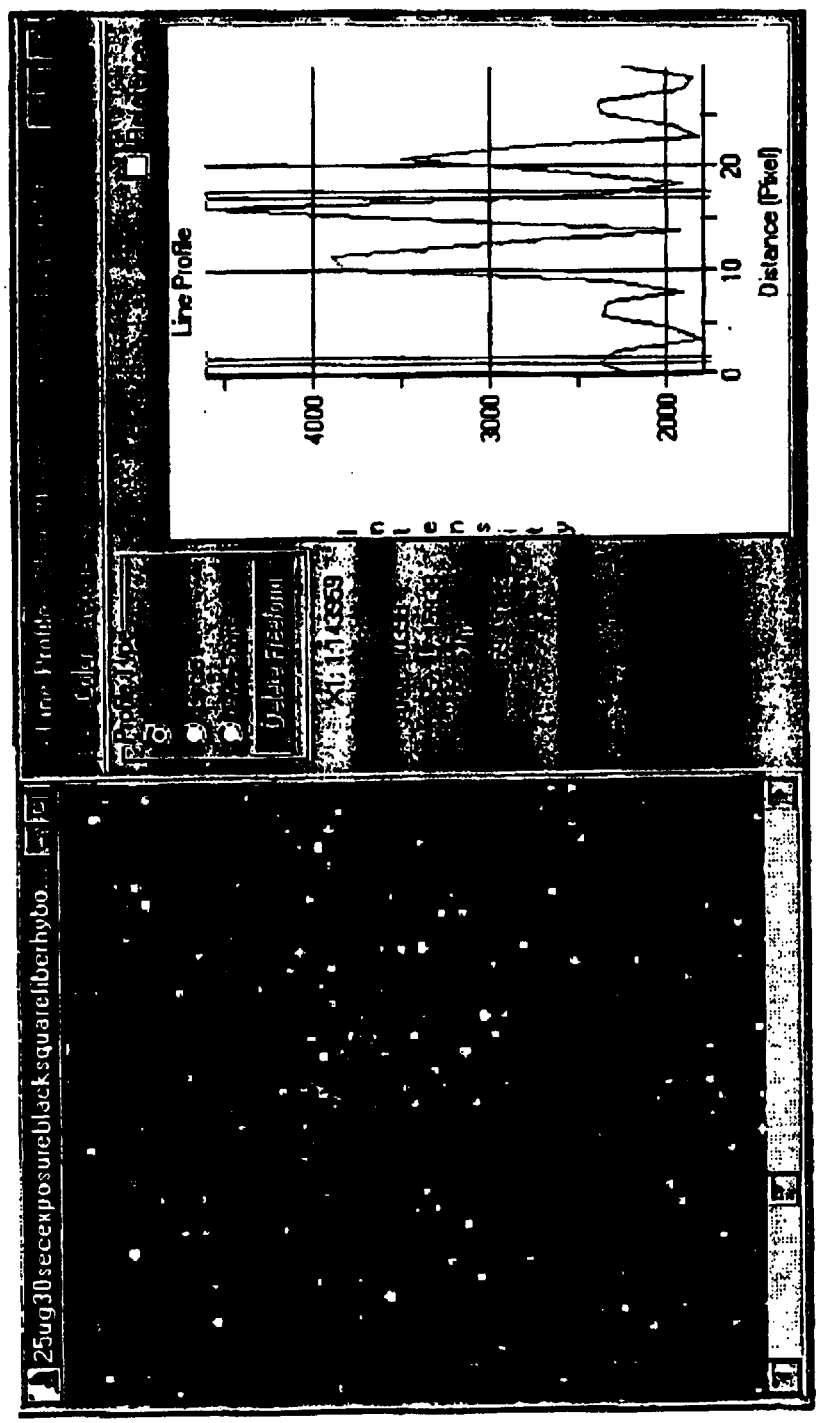
FIG. 2 depicts an image of hybridized fluorescein labeled oligonucleotides to streptavidin-immobilized target analytes (62-mer) on a fiber optic bead array.
Figure 3:
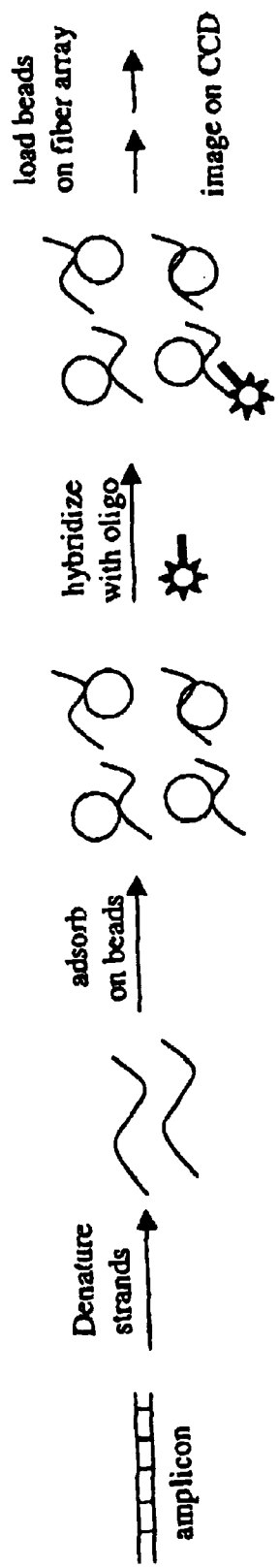
FIG. 3 depicts a flow chart of the experimental design for target analyte immobilization and hybridization to amino-beads.
Figure 4:
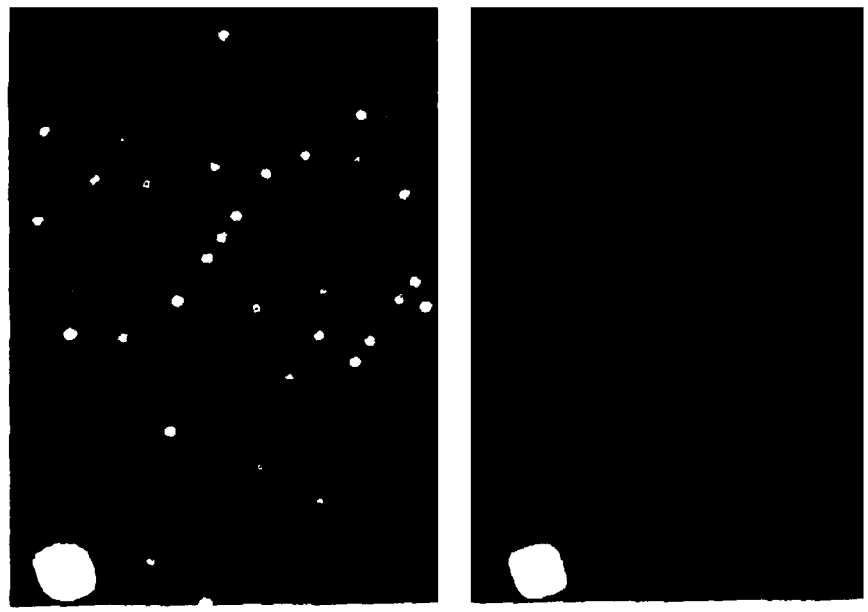
FIG. 4 is an example of an image of FAM-labeled oligonucleotides hybridized to bead immobilized target analytes. A depicts positive control date obtained with the following oligonucleotide: FAM-CCAAGGGTGTGGTGAAAGAT (20-ner) (SEQ ID NO:1). B. depicts negative control data obtained with the following oligonucleotide: FAM-TCCTCCAGACCGCAGGC (17-mer) (SEQ ID NO:2).

Wash once with hybridization buffer.
Load beads on fiber array.
Image on CCD camera system.
A flow chart summarizes the procedure as outlined in FIG. 1. Results are displayed in FIG. 2.

Example 2

Experimental Design for amplicon immobilization and hybridization to amino-beads.
Adsorb known mass (i.e. 100 ng–500 ng) of purified, heat denatured 540-mer amplicon to 1 mg of amino-modified silica solid phase in $dH_{2O}$. (Negative control solid phase= zero nanograms of 70-mer).
Wash beads 2× ($dH_{2O}$) and 1X (0.1 M NaOH) (200 pL).
Wash 1× with Hybridization Buffer (200 μL).
Hybridize with $5\times10^{-7}$ M FAM-labeled complementary oligonucleotide to equilibrium (75 minutes) in 400 mM Na+$HCO_3$/$CO_3$) 5× Denhardts (pH 9.5).
Stringency Wash 2× with Hybridization Buffer (400 mM Na+$HCO_3$/$CO_3$) 5× Denhardts (pH 9.5).
Load fiber array and image on CCD camera.

b) contacting said array composition with a first set of extension probes that hybridize with at least said first target nucleic acid molecules adjacent to a first detection position to from an extension complex;
c) contacting said extension complex with a composition comprising:
  i) at least a frist nucleotide;
  ii) polymerase;
  wherein said polymerase extends a first extension probe with said first nucleotide when said first nucleotide is complementary to said first detection position; and
d) detecting the presence of said first nucleotide, whereby said genotype is determined.

2. The method according to claim 1, wherein said first nucleotide comprises a label.

3. A method of determining the identification of a nucleotide at a detection position in at least a first target nucleir acid molecule comprising:
a) providing an array composition comprising:
  i) a substrate with a surface comprising discrete sites; and

We claim:
1. A method of genotyping comprising:
a) providing an array composition comprising:
  i) a substrate with a surface comprising discrete sites; and
  ii) a population of microspheres comprising at least a first and a second subpopulation, wherein the microspheres of said first subpopulation comprise at least first and second different target nucleic acid molecules from a first individual and the microspheres of said second subpopulation comprise at least first and second different target nucleic acid molecules from a second individual, wherein said at least first and second different target nucleic aicd molecules are covalently attached to each of said microspheres with first and second attachment moieties, respectively; wherein said microspheres are randomly distributed on said surface;
  ii) a population of microspheres comprising at least a first and a second subpopulation, wherein the microspheres of said first subpopulation comprise a plurality of different target nucleic acid molecules from a first individual and the micropheres of said second subpopulation comprise a plurality of different target nucleic acid molecules from a second individual, and wherein a plurality of said different target nucleic acid molecules are covalently attached to each of said microspheres, wherein said microspheres are distribute on said surface;
b) forming a first hybridization complex between said first target nucleic acid molecule and at least a first readout probe, wherein said first target nucleic acid molecule comprises a first and a second target domain, wherein said first hybridization complex comprises said first target nucleic acid molecule, a first readout probe hybridized to said first domain and a second readout probe hybridized to said second domain, wherein at least one of said readout probes comprise a label said determining comprises adding a ligase to form a ligation complex, and c) determining the nucleotide at said detection position.

4. A method of determining the identification of a nucleotide at a detection position in at least a first target nucleic acid molecule comprising:

a) providing an array composition comprising:
 i) a substrate with a surface comprising discrete sites; and
 ii) a population of microspheres comprising at least a first and a second subpopulation, wherein the microspheres of said first subpopulation comprise a plurality of different target nucleic acid molecules from a first individual and the micropheres of said second subpopulation comprise a plurality of different target nucleic acid molecules from a second individual, and wherein a plurality of said different target nucleic acid molecules are covalently attached to each of said microspheres, wherein said microspheres are distribute on said surface;

b) forming a first hybridization complex between said first target nucleic acid molecule and at least a first readout probe;

c) contacting said hybridization complex with at least a first nucleotide and a polymerase, wherein said polymerase extends said first readout probe with said first nucleotide when said first nucleotide is complementary to said first detection position, and d) determining the nucleotide at said detection position.

5. The method according to claim 1, 3, or 4 wherein said substrate is a fiber optic bundle.

6. The method according to claim 1, 3, or 4 wherin said substrate is selected from the group consisting of glass and plastic.

7. The method according to claim 1, 3, or 4 further comprising contacting said microspheres with decoder binding ligands, wherein the microspheres of each subpopulation comprises an identifier binding ligand that will bind a decoder binding ligand for identification and elucidation of said target analyte.

8. A method of genotyping comprising:

a) providing an array composition comprising:
 i) a substrate with a surface comprising discrete sites; and
 ii) a population of microspheres comprising at least a first and a second subpopulation, wherein the microspheres of said first subpopulation comprise at least first and second different target nucleic acid molecules from a first individual and the microspheres of said second subpopulation comprise at least first and second different target nucleic acid molecules from individual, wherein and pluarality of first and second different target nucleic acid molecules are attached to each of said microspheres via receptor-ligand interaction; wherein said target analytes are derivatized with said receptor or said ligand,
 wherein said microspheres are randomly distributed on said surface;

b) contacting said array composition with a first set of extension probes that hybridize with at least said first target nucleic acid molecule adjacent to a first detection position to form an extension complex;

c) contacting said extension complex with a composition comprising
 i) at least a first nucleotide;
 ii) polymerase;
 wherein said polymerase extends a first extension probe with said first nucleotide when said first nucleotide is complementary to said first detection position; and d) detecting the presence of said first nucleotide, whereby said genotype is determined.

9. The method according to claim 8, wherein said reception is streptavidin and said ligand is biotin.

10. The method according to claim 9, wherein said microspheres are streptavidin coated.

* * * * *

UNITED STATES PATENT AND TRADEMARK OFFICE
CERTIFICATE OF CORRECTION

| | |
|---|---|
| PATENT NO. | : 7,285,384 B2 |
| APPLICATION NO. | : 09/785514 |
| DATED | : October 23, 2007 |
| INVENTOR(S) | : Jian-Bing Fan et al. |

It is certified that error appears in the above-identified patent and that said Letters Patent is hereby corrected as shown below:

On the title page item (73) Assignee: please delete "Illuminia" and replace therfore with -- Illumina --

At Column 40, claim 1 b), line 4, please delete "from" and replace therefor with -- form --.

At Column 40, claim 1 c), i), line 7, please delete "frist" and replace therefor with -- first --.

At Column 40, claim 3, line 17, please delete "nucleir" and replace therefor with -- nucleic --.

At Column 41, claim 4 a), ii), line 23, please delete "distribute" and replace therefor with -- distributed --.

At Column 41, claim 5, line 34, please delete "claim" and replace therefor with -- claims --.

At Column 41, claim 6, line 36, please delete "claim 1, 3, or 4 wherin" and replace therefor with -- claims 1, 3, or 4 wherein--.

At Column 41, claim 7, line 39, please delete "claim" and replace therefor with -- claims --.

UNITED STATES PATENT AND TRADEMARK OFFICE
CERTIFICATE OF CORRECTION

PATENT NO.        : 7,285,384 B2
APPLICATION NO.   : 09/785514
DATED             : October 23, 2007
INVENTOR(S)       : Jian-Bing Fan et al.

It is certified that error appears in the above-identified patent and that said Letters Patent is hereby corrected as shown below:

At Column 42, claim 8 a), ii), line 15, please delete "second different target nucleic acid molecules from individual, wherein and pluarality" and replace therefor with -- second different target nucleic acid molecules from a second individual, wherein said plurality --.

At Column 42, claim 9, line 36, please delete "reception" and replace therefor with -- receptor --.

Signed and Sealed this

Twentieth Day of May, 2008

JON W. DUDAS
*Director of the United States Patent and Trademark Office*

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: oligonucleotide with label.

<400> SEQUENCE: 1
ccaagggtgt ggtgaaagat                                        20

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: oligonucleotide with label.

<400> SEQUENCE: 2
tcctccagac cgcaggc                                           17